(12) United States Patent
Jonas et al.

(10) Patent No.: US 6,399,611 B1
(45) Date of Patent: Jun. 4, 2002

(54) ARYLALKYLPYRIDAZINONES

(75) Inventors: Rochus Jonas; Michael Wolf, both of Darmstadt; Norbert Beier, Reinheim, all of (DE)

(73) Assignee: Merck Patent Gesellschaft mit beschraenkter Haftung (DE)

( * ) Notice: Subject to any disclaimer, the term of this patent is extended or adjusted under 35 U.S.C. 154(b) by 0 days.

(21) Appl. No.: 08/634,830

(22) Filed: Apr. 19, 1996

(30) Foreign Application Priority Data

Apr. 20, 1995 (DE) .................... 195 14 568

(51) Int. Cl.⁷ ............... C07D 237/04; A61K 31/501
(52) U.S. Cl. ........................ 514/252; 544/239
(58) Field of Search .................. 544/239; 514/252

(56) References Cited

U.S. PATENT DOCUMENTS

| | | | | |
|---|---|---|---|---|
| 3,682,914 A | * | 8/1972 | Yamamoto et al. | 544/239 |
| 3,975,388 A | * | 8/1976 | Hakim et al. | 544/239 |
| 4,289,774 A | | 9/1981 | Schacht et al. | |
| 4,397,854 A | * | 8/1983 | Sircar | 544/239 |
| 4,666,902 A | | 5/1987 | Zoller et al. | |
| 4,707,481 A | * | 11/1987 | Amschler et al. | 544/239 |
| 4,734,415 A | * | 3/1988 | Sircar et al. | 544/239 |
| 4,816,454 A | | 3/1989 | Zoller et al. | |
| 4,954,499 A | * | 9/1990 | Prucher | 544/239 |
| 5,401,738 A | * | 3/1995 | Mederski et al. | 544/239 |

FOREIGN PATENT DOCUMENTS

| | | |
|---|---|---|
| CA | 2168193 | 7/1996 |
| DE | 19502699 | * 8/1996 |
| EP | 0 186 484 | 7/1986 |
| EP | 0 412 814 | 2/1991 |
| EP | 0 667 158 | 8/1995 |

OTHER PUBLICATIONS

Burger, Medicinal Chemistry, 2d Edition Interscience p. 43, 1960.*
Yamamoto, Chem. Abstr. vol. 72, Entry 100732 abstracting DE 1810200, 1970.*
Pitarch, Eur. J. Med. Chem—Chim. Therap. vol. 9 No. 6 pp. 644–650, 1974.*
L. Pitarch et al., *Eur. J. Med. Chem.—Chimica Therapeutica*, vol. 6, No. 6, pp. 644–646.

* cited by examiner

*Primary Examiner*—John M. Ford
(74) *Attorney, Agent, or Firm*—Millen, White, Zelane & Branigan, P.C.

(57) ABSTRACT

Aralkylpyridazinone derivatives of the formula I

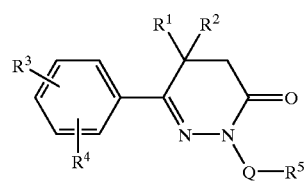

and their physiologically acceptable salts in which
$R^1$, $R^2$, $R^3$, $R^4$, $R^5$ and Q have the meanings indicated in claim 1, show inhibition of phosphodiesterase IV and can be employed for the treatment of inflammatory processes and of allergies, asthma and autoimmune disorders.

10 Claims, No Drawings

ARYLALKYLPYRIDAZINONES

The invention relates to compounds of the formula I

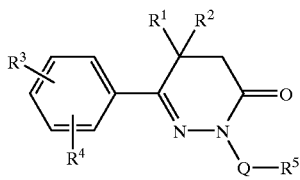

in which
- $R^1$ and $R^2$ in each case independently of one another are H or A,
- $R^3$ and $R^4$ in each case independently of one another are —OH, —$OR^{10}$, —S—$R^{10}$, —$SOR^{10}$, —$SO_2R^{10}$, —$SO_2R^{10}$, Hal, —$NO_2$, —$NH_2$, —$NHR^{10}$ or —$NR^{10}R^{11}$, or together are methylenedioxy,
- $R^5$ is a phenyl radical which is unsubstituted or mono- or disubstituted by $R^6$ and/or $R^7$,
- Q is absent or is alkylene having 1–6 C atoms,
- $R^6$ and $R^7$ in each case independently of one another are —$NH_2$, —$NR^8R^9$, —$NHR^{10}$, —$NR^{10}R^{11}$, —$NO_2$, Hal, —CN, —OA, —COOH or —COOA,
- $R^8$ and $R^9$ in each case independently of one another are H, —COOA, —SO—A, —$SO_2A$, —$CONH_2$, —CONHA, —$CONA_2$, —CO—COOH, —CO—COOA, —CO—$CONH_2$, —CO—CONHA, —CO—$CONA_2$, or acyl, i.e., carboxylic acyl, having 1–8 C atoms which is optionally substituted by 1–5 F and/or Cl atoms,
- A is alkyl preferably having 1 to 6 C atoms which can be substituted by 1–5 F and/or Cl atoms,
- $R^{10}$ and $R^{11}$ in each case independently of one another are A, cycloalkyl having 3–7 C atoms, methylenecycloalkyl having 4–8 C atoms or alkenyl having 2–8 C atoms and
- Hal is F, Cl, Br or I, and their physiologically acceptable salts.

Similar compounds are disclosed in DE 195 02 699.3.

The invention is based on the object of finding novel compounds having useful properties, in particular those which can be used for the production of medicaments.

Upon further study of the specification and appended claims, further objects and advantages of this invention will become apparent to those skilled in the art.

It has been found that the compounds of the formula I and their salts have useful pharmacological properties together with good tolerability. In particular, they show inhibition of phosphodiesterase IV and can be employed for the treatment of asthmatic disorders. The anti-asthmatic action can be determined, for example, by the method of T.Olsson, Acta allergologica 26, 438–447 (1971).

The compounds additionally show an inhibitory action on the formation of TNF (Tumour Necrosis Factor) and are therefore suitable for the treatment of allergic and inflammatory diseases, autoimmune diseases and transplant rejection reactions. They can also be employed for the treatment of memory disorders.

The compounds of the formula I can therefore be used as pharmaceutically active compounds in human and veterinary medicine. They can further be employed as intermediates for the production of other pharmaceutically active compounds.

The invention accordingly relates to the compounds of the formula I and their salts and to a process for the preparation of these compounds and their salts, characterized in that a compound of the formula II

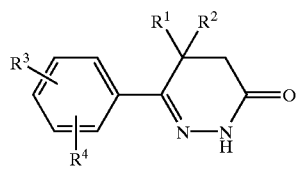

in which
- $R^1$, $R^2$ $R^3$ and $R^4$ have the meanings indicated above, is reacted with a compound of the formula III $$R^5-Q-X \qquad III$$

in which
- $R^5$ and Q have the meanings indicated, and
- X is Cl, Br, OH or a reactive esterified OH group, or in that a compound of the formula IV

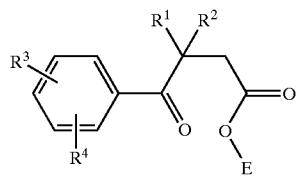

in which
- $R^1$, $R^2$, $R^3$ and $R^4$ have the meanings indicated, and
- E is H or alkyl having 1–4 C atoms, is reacted with a compound of the formula V $$H_2N-NH-Q-R^5 \qquad V$$

in which
- Q and $R^5$ have the meanings indicated, or in that in a compound of the formula I a radical $R^5$ is converted into another radical $R^5$ by reducing a nitro group, alkylating or acylating a primary or a secondary amino group or hydrolyzing a cyano group, and/or in that a compound which corresponds to the formula I, but instead of $R^3$ and/or $R^4$ contains one or two free OH groups, is optionally reacted with a compound of the formula $R^3$—X or $R^4$—X in which $R^3$, $R^4$ and X have the meanings indicated, and/or a base of the formula I is converted into one of its salts by treating with an acid.

Above and below, the radicals $R^1$, $R^2$, $R^3$, $R^4$, $R^5$, Q and X have the meanings indicated in the formulae I, II and III, unless expressly stated otherwise.

A is alkyl.

In the above formulae, alkyl is preferably unbranched and has 1 to 6 C atoms, preferably 1, 2, 3 or 4 C atoms, and is preferably methyl, further preferably ethyl or propyl, furthermore preferably isopropyl, butyl, isobutyl, sec-butyl or tert-butyl, but also n-pentyl or isopentyl.

Cycloalkyl preferably has 3–7 C atoms and is preferably cyclopropyl or cyclobutyl, furthermore preferably cyclopentyl or cyclohexyl, and further also cycloheptyl.

Methylenecycloalkyl preferably has 4–8 C atoms and is preferably methylenecyclopropyl or methylenecyclobutyl, furthermore preferably methylenecyclopentyl or methylenecyclohexyl, and further also methylenecycloheptyl.

Alkenyl is preferably vinyl, 1- or 2-propenyl, 1-butenyl, isobutenyl, sec-butenyl, and is further preferably 1-pentenyl, isopentenyl or 1-hexenyl.

Alkylene is preferably unbranched and is preferably methylene or ethylene, and further preferably propylene or butylene.

Of the radicals $R^1$ and $R^2$, one is preferably H, while the other is preferably propyl or butyl, but particularly preferably ethyl or methyl. R1 and R2 are further preferably together also each hydrogen.

Hal is preferably F, Cl or Br, but also I.

The radicals $R^3$ and $R^4$ can be identical or different and are preferably in the 3- or 4-position of the phenyl ring. They are, for example, independently of one another hydroxyl, —S—$CH_3$, —SO—$CH_3$, —$SO_2CH_3$, F, Cl, Br or I or together methylenedioxy. Particularly preferably, however, they are each methoxy, ethoxy, propoxy, cyclopentoxy, or else fluoro-, difluoro- or trifluoromethoxy, or 1-fluoro-, 2-fluoro-, 1,2-difluoro-, 2,2-difluoro-, 1,2,2-trifluoro- or 2,2,2-trifluoroethoxy.

The radical $R^5$ is preferably phenyl. The phenyl radical is preferably mono- or disubstituted. Preferred substituents are cyano, nitro, amino, acetamido, trifluoroacetamido, methoxy and/or chlorine, also preferred are methylsulfonamido, propionylamino, 2-methylpropionylamino, isobutyrylamino and/or pivalylamino, and further preferred are methoxycarbonylamino, methoxalylamino, ureido and/or carboxyl.

Q—$R^5$ is preferably benzyl, 2-, 3- or 4-nitrobenzyl, 2-, 3- or 4-cyanobenzyl, 2-, 3- or 4-aminobenzyl, 2-, 3- or 4-acetamidobenzyl, 2-, 3- or 4-trifluoroacetamidobenzyl, 2-, 3- or 4-methoxybenzyl, 2-, 3- or 4-chlorobenzyl, is further preferably 2-, 3- or 4-methylsulfonamidobenzyl, 2-, 3- or 4-propionylaminobenzyl, 2-, 3- or 4-(2-methylpropionylamino)-benzyl, 2, 3- or 4-isobutyrylaminobenzyl, 2-, 3- or 4-pivalylaminobenzyl, 2-, 3- or 4-methoxycarbonyl-aminobenzyl, 2-, 3- or 4-ureidobenzyl, 2-, 3- or 4-carboxybenzyl, 2-, 3- or 4-methoxalylaminobenzyl, and is also preferably 2,3-, 2,4-, 2,5-, 2,6-, 3,4- or 3,5-dinitrobenzyl, 2,3-, 2,4-, 2,5-, 2,6-, 3,4- or 3,5-diaminobenzyl, 2,3-, 2,4-, 2,5-, 2,6-3,4- or 3,5-diacetamidobenzyl, 2,3-, 2,4-, 2,5-, 2,6-, 3,4- or 3,5-bis(trifluoroacetamido)benzyl, 2,3-, 2,4-, 2,5-, 2,6-, 3,4- or 3,5-dimethoxybenzyl, 2,3-, 2,4-, 2,5-, 2,6-, 3,4- or 3,5-dichlorobenzyl, 2,3-, 2,4-, 2,5-, 2,6-, 3,4- or 3,5-dimethylsulfonamidobenzyl, 2,3-, 2,4-, 2,5-, 2,6-, 3,4- or 3,5-dipropionylaminobenzyl, 2,3-, 2,4-, 2,5-, 2,6-, 3,4- or 3,5-bis(2-methylpropionylamino)benzyl, 2,3-, 2,4-, 2,5-, 2,6-, 3,4- or 3,5-diisobutyrylaminobenzyl, 2,3-, 2,4-, 2,5-, 2,6-, 3,4- or 3,5-dimethoxycarbonylaminobenzyl, 2,3-, 2,4-, 2,5-, 2,6-, 3,4- or 3,5-dimethoxalylaminobenzyl, 2,3-, 2,4-, 2,5-, 2,6-, 3,4- or 3,5-diureidobenzyl, 2,3-, 2,4-, 2,5-, 2,6-, 3,4- or 3,5-dicarboxybenzyl.

Accordingly, the invention in particular relates to those compounds of the formula I in which at least one of the said radicals has one of the preferred meanings indicated above. Some preferred groups of compounds can be expressed by the following sub-formulae Ia to Ie which correspond to the formula I and in which the radicals which are not described in greater detail have the meaning indicated in the formula I, but in which in Ia $R^1$ is H,
$R^2$ is H or A,
$R^3$ is OA;
in Ib R1 is H,
$R^2$ is methyl or ethyl,
$R^3$ and $R^4$ are each independently of one another
in Ic $R^1$ is H,
$R^2$ is methyl or ethyl,
$R^3$ is OA
$R^4$ is OA where A is mono-, di- or trifluoro-substituted alkyl having 1 to 6 C atoms;
in Id $R^1$ is H,
$R^2$ is methyl or ethyl,
$R^3$ and $R^4$ each independently of one another are $OR^{10}$,
$R^5$ is a mono- or disubstituted phenyl radical;
in Ie $R^1$ and $R^2$ are H,
$R^3$ and $R^4$ each independently of one another are OA and
$R^5$ is a mono- or disubstituted phenyl radical.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; but in particular in DE 19502699.3), namely under reaction conditions which are known and suitable for the said reactions. In this case, use can also be made of variants which are known per se, but not mentioned here in greater detail.

In the compounds of the formulae II and IV, $R^1$, $R^2$, $R^3$ and $R^4$ have the meanings indicated, in particular the preferred meanings indicated.

In the compounds of the formulae III and V, Q is preferably methylene or ethylene, also preferably propylene or butylene.

In the compounds of the formula IV, E is preferably H, methyl or ethyl, and also propyl or butyl.

In the compounds of the formulae III and V, $R^5$ has the preferred meanings indicated, while X is Cl, Br, OH or a reactive esterified OH group.

If X is a reactive esterified OH group, this is preferably alkylsulfonyloxy having 1–6 C atoms (preferably methylsulfonyloxy) or arylsulfonyloxy having 6–10 C atoms (preferably phenyl- or p-tolylsulfonyloxy, and also 2-naphthalenesulfonyloxy)

The starting substances can, if desired, also be formed in situ such that they are not isolated from the reaction mixture, but immediately reacted further to give the compounds of the formula I.

On the other hand, it is possible to carry out the reaction stepwise.

The compounds of the formula I can preferably be obtained by reacting compounds of the formula II with compounds of the formula III.

The starting substances of the formulae II and III are known in some cases. If they are not known, they can be prepared by methods known per se.

Pyridazinones of the formula II are described, for example, in Eur. J. Med. Chem.—Chim. Therapeut. 9, 644–650 (1977).

The compounds of the formula III are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the said reactions. In this case, use can also be made of variants which are known per se, but not mentioned here in greater detail.

In detail, the reaction of the 2,3,4,5-tetrahydropyridazinones with the compounds of the formula III is carried out in the presence or absence of an inert solvent preferably at temperatures from approximately −20 to approximately 150° C., preferably from 20 to 100° C.

Suitable inert solvents are, for example, hydrocarbons such as hexane, petroleum ether, benzene, toluene or xylene; chlorinated hydrocarbons such as trichloroethylene, 1,2-dichloroethane, carbon tetrachloride, chloroform or dichloromethane; alcohols such as methanol, ethanol, isopropanol, n-propanol, n-butanol or tert-butanol; ethers such as diethyl ether, diisopropyl ether, tetrahydrofuran (THF) or dioxanes; glycol ethers such as ethylene glycol monomethyl or monoethyl ether (methyl glycol or ethyl glycol), ethylene glycol dimethyl ether (diglyme), ketones such as acetone or butanone; amides such as acetamide, dimethylacetamide or dimethylformamide (DMF); nitriles such as acetonitrile; sulfoxides such as dimethyl sulfoxide (DMSO); carbon disulfide; carboxylic acids such as formic acid or acetic acid; nitro compounds such as nitromethane or nitrobenzene; esters such as ethyl acetate or mixtures of the said solvents.

The compounds of the formula I can furthermore be obtained by reacting compounds of the formula IV with compounds of the formula V.

In detail, the reaction of the compounds of the formulae IV and V is carried out in the presence or absence of an inert solvent and at temperatures as described above.

The starting substances of the formulae IV and V are known in some cases. If they are not known, they can be prepared by methods known per se.

The compounds of the formulae IV and V are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the said reactions. In this case, use can also be made of variants which are known per se, but not mentioned here in greater detail.

It is also possible in a compound of the formula I to convert a radical $R^5$ into another radical $R^5$, e.g. by reducing nitro groups (for example by hydrogenation on Raney nickel or Pd-carbon in an inert solvent such as methanol or ethanol) to amino groups or hydrolyzing cyano groups to COOH groups. Free amino groups can also be acylated in a customary manner using an acid chloride or anhydride or alkylated using an unsubstituted or substituted alkyl halide, expediently in an inert solvent such as dichloromethane or THF and/or in the presence of a base such as triethylamine or pyridine at temperatures from about −60 to +30° C.

It is also possible to react a compound which corresponds to the formula I, but instead of $R^3$ and/or $R^4$ contains one or two free OH groups, with a compound of the formula $R^3$—X or $R^4$—X in which $R^3$, $R^4$ and X have the meanings indicated. This etherification of the OH groups is carried out by methods known per se, such as are described in the literature (e.g. in the standard works such as Houben-Weyl, Methoden der organischen Chemie [Methods of Organic Chemistry], Georg-Thieme-Verlag, Stuttgart), namely under reaction conditions which are known and suitable for the said reactions. In this case, use can also be made of variants which are known per se, but not mentioned here in greater detail.

Further, a base of the formula I can be converted into the associated acid addition salt using an. acid, for example by reaction of equivalent amounts of the base and of the acid in an inert solvent such as ethanol and subsequent evaporation. For this reaction, suitable acids are in particular those which give physiologically acceptable salts. Inorganic ,acids can thus be used, e.g. sulfuric acid, nitric acid, hydrohalic acids such as hydrochloric acid or hydrobromic acid, phosphoric acids such as orthophosphoric acid, sulfamic acid, also organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids and laurylsulfuric acid. Salts with physiologically unacceptable acids, e.g. picrates, can be used for the isolation and/or purification of the compounds of the formula I.

On the other hand, if desired, the free bases of the formula I can be liberated from their salts using bases (e.g. sodium or potassium hydroxide or carbonates).

Compounds of the formula I can contain one or more centers of asymmetry. In this case, they usually exist in racemic form. Racemates which are obtained can be separated into their enantiomers mechanically or chemically by methods known per se. Preferably, diastereomers are formed from the racemic mixture by reaction with an optically active resolving agent.

Of course, it is also possible to obtain optically active compounds of the formula I by the methods described above, by using starting substances which are already optically active.

The formula I includes all stereoisomers and their mixtures, e.g. the racemates.

The invention also relates to the use of the compounds of the formula I and/or their physiologically acceptable salts for the production of pharmaceutical preparations, in particular by a non-chemical route. In this context, they can be brought into a suitable dose form together with at least one solid, liquid and/or semi-liquid excipient or auxiliary and if appropriate in combination with one or more other active compounds.

The invention also relates to medicaments of the formula I and their physiologically acceptable salts as phosphodiesterase IV inhibitors.

In this context, the substances according to the invention are generally administered in analogy to known substances having a phosphodiesterase inhibiting effect, such as aminophylline preferably in doses of between about 1 and 100 mg, in particular between 2 and 20 mg, per dosage unit.

The daily dose is preferably from about 0.2 to 20 mg/kg of body weight. The specific dose for each individual patient, however, depends on a wide variety of factors, for example the activity of the specific compound employed, the age, body weight, general state of health, sex and diet of the patent, the time and route of administration, the rate of excretion, the combination of pharmaceutical substances and the severity of the particular disease which s the subject of the therapy. Oral administration is preferred. In comparison with the digitalis glycosides used to date for the therapy of cardiac insufficiency, the compounds of the formula I are distinguished by enhanced therapeutic breadth and peripheral relief.

The invention further relates to pharmaceutical preparations, comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration or topical application and do not react with the novel compounds, for example water, vegetable oils, benzyl alcohols, alkylene glycols, polyethylene glycols, glycerol triacetate, gelatin, carbohydrates such as lactose or starch, magnesium stearate, talc and petroleum jelly. Tablets, pills, coated tablets, capsules, powders, granules, syrups, juices or drops are used in particular for oral administration, suppositories for rectal administration, solutions, preferably oily or aqueous solutions, and also suspensions, emulsions or implants for parenteral administration, and ointments, creams or powders for topical application. The novel compounds can also be lyophilized and the lyophilizates obtained used, for example, for the production of injection preparations. The preparations indicated can be sterilized and/or contain auxiliaries such as lubricants, preservatives, stabilizers and/or wetting agents, emulsifiers, salts for affecting the osmotic pressure, buffer substances, colorants, flavorings and/or one or more other active compounds, e.g. one or more vitamins.

The compounds of the formula I and their physiologically acceptable salts can also be employed in the control of illnesses in which an increase in the cAMP (cyclic adenosine monophosphate) level leads to inhibition or prevention of inflammation and muscle relaxation. The compounds according to the invention can be used, in particular, in the treatment of allergies, asthma, chronic bronchitis, atopic dermatitis, psoriasis and other skin diseases and autoimmune disorders.

The entire disclosure of all applications, patents and publications, cited above and below, and of corresponding German application No. DE 195 14 568.2, filed Apr. 20, 1995, are hereby incorporated by reference.

Above and below, all temperatures are indicated in ° C. In the following examples, "customary working up" means: water is added, if necessary, the mixture is adjusted, if necessary, depending on the constitution of the final product, to pH values from 2 to 10 and extracted with ethyl acetate or dichloromethane, and the organic phase is separated off, dried over sodium sulfate, evaporated and purified by chromatography on silica gel and/or by crystallization.

In the foregoing and in the following examples, all temperatures are set forth uncorrected in degrees Celsius; and, unless otherwise indicated, all parts and percentages are by weight.

EXAMPLES

Example 1

A suspension of 4.70 g of 6-(3,4-dimethoxy-phenyl)-2,3,4,5-tetrahydropyridazin-3-one ("A") in 150 ml of THF is treated with 2.24 g of potassium tert-butoxide and stirred for 30 minutes. 4.32 g of 4-nitro-benzyl chloride are added thereto and the mixture is stirred at room temperature for 10 hours. The solvent is removed and the residue is worked up in the customary manner. 2-(4-Nitrobenzyl)-6-(3,4-dimethoxy-phenyl)-2,3,4,5-tetrahydropyridazin -3-one, m.p. 126°, is obtained.

The following are obtained analogously by reaction of "A"
with 3-nitrobenzyl chloride:
   2-(3-nitrobenzyl)-6-(3,4-dimethoxyphenyl)-2,3,4,5-tetrahydropyridazin-3-one, m.p. 122°;
with, 2-nitrobenzyl chloride:
   2-(2-nitrobenzyl)-6-(3,4-dimethoxyphenyl)-2,3,4,5-tetrahydropyridazin-3-one;
with 2,3-dinitrobenzyl chloride:
   2-(2,3-dinitrobenzyl)-6-(3,4-dimethoxyphenyl)-2,3,4,5-tetrahydropyridazin-3-one;
with 2,4-dinitrobenzyl chloride:
   2-(2,4-dinitrobenzyl)-6-(3,4-dimethoxyphenyl)-2,3,4,5-tetrahydropyridazin-3-one;
with 2-methoxybenzyl chloride:
   2-(2-methoxybenzyl)-6-(3,4-dimethoxyphenyl)-2,3,4,5-tetrahydropyridazin-3-one;
with 4-methoxybenzyl chloride:
   2-(4-methoxybenzyl)-6-(3,4-dimethoxyphenyl)-2,3,4,5-tetrahydropyridazin-3-one;
with 2-chlorobenzyl chloride:
   2-(2-chlorobenzyl)-6-(3,4-dimethoxyphenyl)-2,3,4,5-tetrahydropyridazin-3-one;
with 2,6-dichlorobenzyl chloride:
   2-(2,6-dichlorobenzyl)-6-(3,4-dimethoxyphenyl)-2,3,4,5-tetrahydropyridazin-3-one;
with 4-cyanobenzyl chloride:
   2-(4-cyanobenzyl)-6-(3,4-dimethoxyphenyl)-2,3,4,5-tetrahydropyridazin-3-one;
with 4-carboxybenzyl chloride:
   2-(4-carboxybenzyl)-6-(3,4-dimethoxyphenyl)-2,3,4,5-tetrahydropyridazin-3-one.

Example 2

Analogously to Example 1, by reaction of 6-(3,4-dimethoxyphenyl)-5-ethyl-2,3,4,5-tetrahydropyridazin-3-one ("B") with 4-nitrobenzyl chloride 2-(4-nitrobenzyl)-6-(3,4-dimethoxyphenyl)-5-ethyl-2,3,4,5-tetrahydropyridazin-3-one is obtained.

The following are obtained analogously by reaction of "B"
with 3-nitrobenzyl chloride: 2-(3-nitrobenzyl)-6-(3,4-dimethoxyphenyl)-5-ethyl-2,3,4,5-tetrahydropyridazin-3-one;
with 2-nitrobenzyl chloride:
   2-(2-nitrobenzyl)-6-(3,4-dimethoxyphenyl)-5-ethyl-2,3,4,5-tetrahydropyridazin-3-one;
with 2,3-dinitrobenzyl chloride:
   2-(2, 3-dinitrobenzyl)-6-(3, 4-dimethoxyphenyl)-5-ethyl-2,3,4,5-tetrahydropyridazin-3-one;
with 2,4-dinitrobenzyl chloride:
   2-(2,4-dinitrobenzyl)-6-(3,4-dimethoxyphenyl)-5-ethyl-2,3,4,5-tetrahydropyridazin-3-one;
with 2-methoxybenzyl chloride:
   2-(2-methoxybenzyl)-6-(3,4-dimethoxyphenyl)-5-ethyl-2,3,4,5-tetrahydropyridazin-3-one;
with 4-methoxybenzyl chloride:
   2-(4-methoxybenzyl)-6-(3,4-dimethoxyphenyl)-5-ethyl-2,3,4,5-tetrahydropyridazin-3-one;
with 2-chlorobenzyl chloride:
   2-(2-chlorobenzyl)-6-(3,4-dimethoxyphenyl)-5-ethyl-2,3,4,5-tetrahydropyridazin-3-one;
with 2,6-dichlorobenzyl chloride:
   2-(2,6-dichlorobenzyl)-6-(3,4-dimethoxyphenyl)-5-ethyl-2,3,4,5-tetrahydropyridazin-3-one;
with 4-cyanobenzyl chloride:
   2-(4-cyanobenzyl)-6-(3,4-dimethoxyphenyl)-5-ethyl-2,3,4,5-tetrahydropyridazin-3-one;
with 4-carboxybenzyl chloride:
   2-(4-carboxybenzyl)-6-(3,4-dimethoxyphenyl)-5-ethyl-2,3,4,5-tetrahydropyridazin-3-one.

Example 3

Analogously to Example 1, by reaction of 6-(3-methoxy-4-trifluoromethoxyphenyl)-5-ethyl-2,3,4,5- tetrahydropyridazin-3-one ("B") with 4-nitrobenzyl chloride ("C") 2-(4-nitrobenzyl)-6-(3-methoxy-4-trifluoromethoxyphenyl)-5-ethyl-2,3,4,5-tetrahydropyridazin-3-one is obtained.

The following are obtained analogously by reaction of "C"

with 6-(3-methoxy-4-difluoromethoxyphenyl)-5-ethyl-2,3,4,5-tetrahydropyridazin-3-one:
    2-(4-nitrobenzyl)-6-(3-methoxy-4-difluoromethoxyphenyl)-5-ethyl-2,3,4,5-tetrahydropyridazin-3-one;

with 6-(3-methoxy-4-fluoromethoxyphenyl)-5-ethyl-2,3,4,5-tetrahydropyridazin-3-one:
    2-(4-nitrobenzyl)-6-(3-methoxy-4-fluoromethoxyphenyl)-5-ethyl-2,3,4,5-tetrahydropyridazin-3-one;

with 6-(3-difluoromethoxy-4-methoxyphenyl)-5-ethyl-2,3,4,5-tetrahydropyridazin-3-one:
    2-(4-nitrobenzyl)-6-(3-difluoromethoxy-4-methoxyphenyl)-5-ethyl-2,3,4,5-tetrahydropyridazin-3-one;

with 6-(3-trifluoromethoxy-4-methoxyphenyl)-5-ethyl-2,3,4,5-tetrahydropyridazin-3-one:
    2-(4-nitrobenzyl)-6-(3-trifluoromethoxy-4-methoxyphenyl)-5-ethyl-2,3,4,5-tetrahydropyridazin-3-one;

with 6-(3-fluoromethoxy-4-methoxyphenyl)-5-ethyl-2,3,4,5-tetrahydropyridazin-3-one:
    2-(4-nitrobenzyl)-6-(3-fluoromethoxy-4-methoxyphenyl)-5-ethyl-2,3,4,5-tetrahydropyridazin-3-one;

with 6-(3-methoxy-4-ethoxyphenyl)-5-ethyl-2,3,4,5-tetrahydropyridazin-3-one:
    2-(4-nitrobenzyl)-6-(3-methoxy-4-ethoxyphenyl)-5-ethyl-2,3,4,5-tetrahydropyridazin-3-one;

with 6-(3-ethoxy-4-methoxyphenyl)-5-ethyl-2,3,4,5-tetrahydropyridazin-3-one:
    2-(4-nitrobenzyl)-6-(3-ethoxy-4-methoxyphenyl)-5-ethyl-2,3,4,5-tetrahydropyridazin-3-one;

with 6-(3-hydroxy-4-methoxyphenyl)-5-ethyl-2,3,4,5-tetrahydropyridazin-3-one:
    2-(4-nitrobenzyl)-6-(3-hydroxy-4-methoxyphenyl)-5-ethyl-2,3,4,5-tetrahydropyridazin-3-one;

with 6-(4-methylsulfonylphenyl)-5-ethyl-2,3,4,5-tetrahydropyridazin-3-one:
    2-(4-nitrobenzyl)-6-(4-methylsulfonylphenyl)-5-ethyl-2,3,4,5-tetrahydropyridazin-3-one;

with 6-(4-methylenoxyphenyl)-5-ethyl-2,3,4,5-tetrahydropyridazin-3-one:
    2-(4-nitrobenzyl)-6-(4-methylenoxyphenyl)-5-ethyl-2,3,4,5-tetrahydropyridazin-3-one;

with 6-(3-cyclopentyloxy-4-methoxy)-5-ethyl-2,3,4,5-tetrahydropyridazin-3-one:
    2-(4-nitrobenzyl)-6-(3-cyclopentyloxy-4-methoxyphenyl)-5-ethyl-2,3,4,5-tetrahydropyridazin-3-one.

Example 4

A solution of 4.6 g of 2-(4-nitrobenzyl)-6-(3,4-dimethoxyphenyl)-2,3,4,5-tetrahydropyridazin-3-one in 60 ml of methanol is hydrogenated in the presence of Raney nickel. The catalyst is filtered off and the solution concentrated. After recrystallization, 2-(4-aminobenzyl)-6-(3,4-dimethoxyphenyl)-2,3,4,5-tetrahydropyridazin-3-one, m.p. 184°, is obtained.

The following are obtained analogously by hydrogenation of 2-(3-nitrobenzyl)-6-(3,4-dimethoxyphenyl)-2,3,4,5-tetrahydropyridazin-3-one:
    2-(3-aminobenzyl)-6-(3, 4-dimethoxyphenyl)-2,3,4,5-tetrahydropyridazin-3-one, m.p. 140°;

of 2-(2-nitrobenzyl)-6-(3,4-dimethoxyphenyl)-2,3,4,5-tetrahydropyridazin-3-one:
    2-(2-aminobenzyl)-6-(3,4-dimethoxyphenyl)-2,3,4,5-tetrahydropyridazin-3-one;

of 2-(2,3-dinitrobenzyl)-6-(3,4-dimethoxyphenyl)-2,3,4,5-tetrahydropyridazin-3-one:
    2-(2,3-diaminobenzyl)-6-(3,4-dimethoxyphenyl)-2,3,4,5-tetrahydropyridazin-3-one;

of 2-(2, 4-dinitrobenzyl)-6-(3, 4-dimethoxyphenyl)-2,3,4,5-tetrahydropyridazin-3-one:
    2-(2,4-diaminobenzyl)-6-(3,4-dimethoxyphenyl)-2,3,4,5-tetrahydropyridazin-3-one;

of 2-(4-nitrobenzyl)-6-(3,4-dimethoxyphenyl)-5-ethyl-2,3,4,5-tetrahydropyridazin-3-one:
    2-(4-aminobenzyl)-6-(3,4-dimethoxyphenyl)-5-ethyl-2,3,4,5-tetrahydropyridazin-3-one;

of 2-(3-nitrobenzyl)-6-(3,4-dimethoxyphenyl)-5-ethyl-2,3,4,5-tetrahydropyridazin-3-one:
    2-(3-aminobenzyl)-6-(3,4-dimethoxyphenyl)-5-ethyl-2,3,4,5-tetrahydropyridazin-3-one, m.p. 49°;

of 2-(2-nitrobenzyl)-6-(3,4-dimethoxyphenyl)-5-ethyl-2,3,4,5-tetrahydropyridazin-3-one:
    2-(2-aminobenzyl)-6-(3,4-dimethoxyphenyl)-5-ethyl-2,3,4,5-tetrahydropyridazin-3-one;

of 2-(2,3-dinitrobenzyl)-6-(3,4-dimethoxyphenyl)-5-ethyl-2,3,4,5-tetrahydropyridazin-3-one:
    2-(2,3-diaminobenzyl)-6-(3,4-dimethoxyphenyl)-5-ethyl-2,3,4,5-tetrahydropyridazin-3-one;

of 2-(2,4-dinitrobenzyl)-6-(3,4-dimethoxyphenyl)-5-ethyl-2,3,4,5-tetrahydropyridazin-3-one:
    2-(2,4-diaminobenzyl)-6-(3,4-dimethoxyphenyl)-5-ethyl-2,3,4,5-tetrahydropyridazin-3-one;

of 2-(4-nitrobenzyl)-6-(3-methoxy-4-trifluoromethoxyphenyl)-5-ethyl-2,3,4,5-tetrahydropyridazin-3-one:
    2-(4-aminobenzyl)-6-(3-methoxy-4-trifluoromethoxyphenyl)-5-ethyl-2,3,4,5-tetrahydropyridazin-3-one;

of 2-(4-nitrobenzyl)-6-(3-methoxy-4-difluoromethoxyphenyl)-5-ethyl-2,3,4,5-tetrahydropyridazin-3-one:
    2-(4-aminobenzyl)-6-(3-methoxy-4-difluoromethoxyphenyl)-5-ethyl-2,3,4,5-tetrahydropyridazin-3-one;

of 2-(4-nitrobenzyl)-6-(3-methoxy-4-fluoromethoxyphenyl)-5-ethyl-2,3,4,5-tetrahydropyridazin-3-one:
    2-(4-aminobenzyl)-6-(3-methoxy-4-fluoromethoxyphenyl)-5-ethyl-2,3,4,5-tetrahydropyridazin-3-one;

of 2-(4-nitrobenzyl)-6-(3-difluoromethoxy-4-methoxyphenyl)-5-ethyl-2,3,4,5-tetrahydropyridazin-3-one:
    2-(4-aminobenzyl)-6-(3-difluoromethoxy-4-methoxyphenyl)-5-ethyl-2,3,4,5-tetrahydropyridazin-3-one;

of 2-(4-nitrobenzyl)-6-(3-trifluoromethoxy-4-methoxyphenyl)-5-ethyl-2,3,4,5-tetrahydropyridazin-3-one:
    2-(4-aminobenzyl)-6-(3-trifluoromethoxy-4-methoxyphenyl)-5-ethyl-2, 3,4, 5-tetrahydropyridazin-3-one;

of 2-(4-nitrobenzyl)-6-(3-fluoromethoxy-4-methoxyphenyl)-5-ethyl-2,3,4,5-tetrahydropyridazin-3-one:

2-(4-aminobenzyl)-6-(3-fluoromethoxy-4-methoxyphenyl)-5-ethyl-2,3,4,5-tetrahydropyridazin-3-one;

of 2-(4-nitrobenzyl)-6-(3-methoxy-4-ethoxyphenyl)-5-ethyl-2,3,4,5-tetrahydropyridazin-3-one:

2-(4-aminobenzyl)-6-(3-methoxy-4-ethoxyphenyl)-5-ethyl-2,3,4,5-tetrahydropyridazin-3-one;

of 2-(4-nitrobenzyl)-6-(3-ethoxy-4-methoxyphenyl)-5-ethyl-2,3,4,5-tetrahydropyridazin-3-one:

2-(4-aminobenzyl)-6-(3-ethoxy-4-methoxyphenyl)-5-ethyl-2,3,4,5-tetrahydropyridazin-3-one;

of 2-(4-nitrobenzyl)-6-(3-hydroxy-4-methoxyphenyl)-5-ethyl-2,3,4,5-tetrahydropyridazin-3-one:

2-(4-aminobenzyl)-6-(3-hydroxy-4-methoxyphenyl)-5-ethyl-2,3,4,5-tetrahydropyridazin-3-one;

of 2-(4-nitrobenzyl)-6-(4-methylsulfonylphenyl)-5-ethyl-2,3,4,5-tetrahydropyridazin-3-one:

2-(4-aminobenzyl)-6-(4-methylsulfonylphenyl)-5-ethyl-2,3,4,5-tetrahydropyridazin-3-one;

of 2-(4-nitrobenzyl)-6-(4-methylenoxyphenyl)-5-ethyl-2,3,4,5-tetrahydropyridazin-3-one:

2-(4-aminobenzyl)-6-(4-methylenoxyphenyl)-5-ethyl-2,3,4,5-tetrahydropyridazin-3-one;

of 2-(4-nitrobenzyl)-6-(3-cyclopentyloxy-4-methoxyphenyl)-5-ethyl-2,3,4,5-tetrahydropyridazin-3-one:

2-(4-aminobenzyl)-6-(3-cyclopentyloxy-4-methoxyphenyl)-5-ethyl-2,3,4,5-tetrahydropyridazin-3-one;

of 2-(3-nitrobenzyl)-6-(3-cyclopentyloxy-4-methoxyphenyl)-5-ethyl-2,3,4,5-tetrahydropyridazin-3-one:

2-(3-aminobenzyl)-6-(3-cyclopentyloxy-4-methoxyphenyl)-5-ethyl-2,3,4,5-tetrahydropyridazin-3-one, m.p. 109°;

of 2-(4-nitrophenethyl)-6-(3,4-dimethoxyphenyl)-2,3,4,5-tetrahydropyridazin-3-one:

2-(4-aminophenethyl)-6-(3,4-dimethoxyphenyl)-2,3,4,5-tetrahydropyridazin-3-one;

of 2-(4-nitrophenethyl)-6-(3,4-dimethoxyphenyl)-5-ethyl-2,3,4,5-tetrahydropyridazin-3-one:

2-(4-aminophenethyl)-6-(3,4-dimethoxyphenyl)-5-ethyl-2,3,4,5-tetrahydropyridazin-3-one;

of 2-(3-nitrobenzyl)-6-(3-ethoxy-4-methoxyphenyl)-2,3,4,5-tetrahydropyridazin-3-one:

2-(3-aminobenzyl)-6-(3-ethoxy-4-methoxyphenyl)-2,3,4,5-tetrahydropyridazin-3-one, m.p. 112°.

Example 5

10 g of 2-(4-cyanobenzyl)-6-(3,4-dihydroxyphenyl)-5-ethyl-2,3,4,5-tetrahydropyridazin-3-one are added with stirring to a cooled solution of 1.2 g of NaOH in 100 ml of water and the mixture is subsequently stirred for 10 hours. It is warmed cautiously and a stream of air is passed through the solution. Cooled sulfuric acid and water are then added. The mixture is worked up in the customary manner and 2-(4-carboxybenzyl)-6-(3,4-dihydroxyphenyl)-5-ethyl-2,3,4,5-tetrahydropyridazin-3-one is obtained.

Example 6

A solution of 3.0 g of 2-(4-aminobenzyl)-6-(3,4-dimethoxyphenyl)-2,3,4,5-tetrahydropyridazin-3-one ("D") and 0.75 ml of pyridine in 80 ml of dichloromethane is treated with 1.0 g of butyryl chloride and subsequently stirred for 1 hour. The solvent is removed and the residue is worked up in the customary manner. After recrystallization, 2-(4-butyrylaminobenzyl)-6-(3,4-dimethoxyphenyl)-2,3,4,5-tetrahydropyridazin-3-one, m.p. 148°, is obtained.

The following are obtained analogously by reaction of "D"

with acetyl chloride:

2-(4-acetamidobenzyl)-6-(3,4-dimethoxyphenyl)-2,3,4,5-tetrahydropyridazin-3-one, m.p. 183°;

with trifluoroacetyl chloride:

2-(4-trifluoroacetamidobenzyl)-6-(3,4-dimethoxyphenyl)-2,3,4,5-tetrahydropyridazin-3-one, m.p. 210°;

with methylsulfonyl chloride:

2-(4-methylsulfonamidobenzyl)-6-(3,4-dimethoxyphenyl)-2,3,4,5-tetrahydropyridazin-3-one, m.p. 138°;

with propionyl chloride:

2-(4-propionylaminobenzyl)-6-(3,4-dimethoxyphenyl)-2,3,4,5-tetrahydropyridazin-3-one, m.p. 176°;

with 2,2-dimethylpropionyl chloride:

2-(4-tert-butylcarbonylaminobenzyl)-6-(3,4-dimethoxyphenyl)-2,3,4,5-tetrahydropyridazin-3-one, m.p. 155°;

with isobutyryl chloride:

2-(4-isobutyrylaminobenzyl)-6-(3,4-dimethoxyphenyl)-2,3,4,5-tetrahydropyridazin-3-one;

with methyl chloroformate:

2-(4-methoxycarbonylaminobenzyl)-6-(3,4-dimethoxyphenyl)-2,3,4,5-tetrahydropyridazin-3-one;

with pivalyl chloride:

2-(4-pivalylaminobenzyl)-6-(3, 4-dimethoxyphenyl)-2,3,4,5-tetrahydropyridazin-3-one;

with cyclopentanecarbonyl chloride:

2-(4-cyclopentylcarbamoylbenzyl)-6-(3,4-dimethoxyphenyl)-2,3,4,5-tetrahydropyridazin-3-one;

with ethyl chloroformate:

2-(4-ethoxycarbonylaminobenzyl)-6-(3,4-dimethoxyphenyl)-2,3,4,5-tetrahydropyridazin-3-one, m.p. 147°;

with methoxalyl chloride:

2-(4-methoxalylaminobenzyl)-6-(3,4-dimethoxyphenyl)-2,3,4,5-tetrahydropyridazin-3-one;

with chloroformamide:

2-(4-ureidobenzyl)-6-(3,4-dimethoxyphenyl)-2,3,4,5-tetrahydropyridazin-3-one;

with pentanoyl chloride:

2-(4-pentanoylaminobenzyl)-6-(3,4-dimethoxyphenyl)-2,3,4,5-tetrahydropyridazin-3-one;

with hexanoyl chloride:

2-(4-hexanoylaminobenzyl)-6-(3,4-dimethoxyphenyl)-2,3,4,5-tetrahydropiridazin-3-one;

with pentafluoropropionyl chloride:

2-(4-pentafluoropropionylaminobenzyl)-6-(3,4-dimethoxyphenyl)-2,3,4,5-tetrahydropyridazin-3-one.

The following are obtained analogously by reaction of 2-(4-aminobenzyl)-6-(3,4-dimethoxyphenyl)-5-ethyl-2,3,4,5-tetrahydropyridazin-3-one with acetyl chloride:

2-(4-acetamidobenzyl)-6-(3,4-dimethoxyphenyl)-5-ethyl-2,3,4,5-tetrahydropyridazin-3-one;

with trifluoroacetyl chloride:
  2-(4-trifluoroacetamidobenzyl)-6-(3,4-dimethoxyphenyl)-5-ethyl-2,3,4,5-tetrahydropyridazin-3-one, m.p. 133°;
with methylsulfonyl chloride:
  2-(4-methylsulfonamidobenzyl)-6-(3,4-dimethoxyphenyl)-5-ethyl-2,3,4,5-tetrahydropyridazin-3-one;
with propionyl chloride:
  2-(4-propionylaminobenzyl)-6-(3,4-dimethoxyphenyl)-5-ethyl-2,3,4,5-tetrahydropyridazin-3-one, m.p. 81°
with 2,2-dimethylpropionyl chloride:
  2-(4-tert-butylcarbonylaminobenzyl)-6-(3,4-dimethoxyphenyl)-5-ethyl-2,3,4,5-tetrahydropyridazin-3-one;
with butyryl chloride:
  2-(4-butyrylaminobenzyl)-6-(3,4-dimethoxyphenyl)-5-ethyl-2,3,4,5-tetrahydropyridazin-3-one, m.p. 117°;
with isobutyryl chloride:
  2-(4-isobutyrylaminobenzyl)-6-(3,4-dimethoxyphenyl)-5-ethyl-2,3,4,5-tetrahydropyridazin-3-one;
with methyl chloroformate:
  2-(4-methoxycarbonylaminobenzyl)-6-(3,4-dimethoxyphenyl)-5-ethyl-2,3,4,5-tetrahydropyridazin-3-one, m.p. 144°;
with pivalyl chloride:
  2-(4-pivalylaminobenzyl)-6-(3,4-dimethoxyphenyl)-5-ethyl-2,3,4,5-tetrahydropyridazin-3-one;
with cyclopentanecarbonyl chloride:
  2-(4-cyclopentylcarbamoylbenzyl)-6-(3,4-dimethoxyphenyl)-5-ethyl-2,3,4,5-tetrahydropyridazin-3-one;
with ethyl chloroformate:
  2-(4-ethoxycarbonylaminobenzyl)-6-(3,4-dimethoxyphenyl)-5-ethyl-2,3,4,5-tetrahydropyridazin-3-one, m.p. 154°;
with methoxalyl chloride:
  2-(4-methoxalylaminobenzyl)-6-(3,4-dimethoxyphenyl)-5-ethyl-2,3,4,5-tetrahydropyridazin-3-one;
with chloroformamide:
  2-(4-ureidobenzyl)-6-(3,4-dimethoxyphenyl)-5-ethyl-2,3,4,5-tetrahydropyridazin-3-one;
with pentanoyl chloride:
  2-(4-pentanoylaminobenzyl)-6-(3,4-dimethoxyphenyl)-5-ethyl-2,3,4,5-tetrahydropyridazin-3-one;
with hexanoyl chloride:
  2-(4-hexanoylaminobenzyl)-6-(3,4-dimethoxyphenyl)-5-ethyl-2,3,4,5-tetrahydropyridazin-3-one;
with pentafluoropropionyl chloride:
  2-(4-pentafluoropropionylaminobenzyl)-6-(3,4-dimethoxyphenyl)-5-ethyl-2,3,4,5-tetrahydropyridazin-3-one.

The following are obtained analogously by reaction of 2-(4-aminobenzyl)-6-(3-ethoxy-4-methoxyphenyl)-5-ethyl-2,3,4,5-tetrahydropyridazin-3-one
with acetyl chloride:
  2-(4-acetamidobenzyl)-6-(3-ethoxy-4-methoxyphenyl)-5-ethyl-2,3,4,5-tetrahydropyridazin-3-one;
with trifluoroacetyl chloride:
  2-(4-trifluoroacetamidobenzyl)-6-(3-ethoxy-4-methoxyphenyl)-5-ethyl-2,3,4,5-tetrahydropyridazin-3-one;
with methylsulfonyl chloride:
  2-(4-methylsulfonamidobenzyl)-6-(3-ethoxy-4-methoxyphenyl)-5-ethyl-2,3,4,5-tetrahydropyridazin-3-one;
with propionyl chloride:
  2-(4-propionylaminobenzyl)-6-(3-ethoxy-4-methoxyphenyl)-5-ethyl-2,3,4,5-tetrahydropyridazin-3-one;
with butyryl chloride:
  2-(4-butyrylaminobenzyl)-6-(3-ethoxy-4-methoxyphenyl)-5-ethyl-2,3,4,5-tetrahydropyridazin-3-one;
with isobutyryl chloride:
  2-(4-isobutyrylaminobenzyl)-6-(3-ethoxy-4-methoxyphenyl)-5-ethyl-2,3,4,5-tetrahydropyridazin-3-one;
with methyl chloroformate:
  2-(4-methoxycarbonylaminobenzyl)-6-(3-ethoxy-4-methoxyphenyl)-5-ethyl-2,3,4,5-tetrahydropyridazin-3-one;
with pivalyl chloride:
  2-(4-pivalylaminobenzyl)-6-(3-ethoxy-4-methoxyphenyl)-5-ethyl-2,3,4,5-tetrahydropyridazin-3-one
with cyclopentanecarbonyl chloride:
  2-(4-cyclopentylcarbamoylbenzyl)-6-(3-ethoxy-4-methoxyphenyl)-5-ethyl-2,3,4,5-tetrahydropyridazin-3-one;
with ethyl chloroformate:
  2-(4-ethoxycarbonylaminobenzyl)-6-(3-ethoxy-4-methoxyphenyl)-5-ethyl-2,3,4,5-tetrahydropyridazin-3-one;
with methoxalyl chloride:
  2-(4-methoxalylaminobenzyl)-6-(3-ethoxy-4-methoxyphenyl)-5 -ethyl-2,3,4,5-tetrahydropyridazin-3-one;
with chloroformamide:
  2-(4-ureidobenzyl)-6-(3-ethoxy-4-methoxyphenyl)-5-ethyl-2,3,4,5-tetrahydropyridazin-3-one;
with pentanoyl chloride:
  2-(4-pentanoylaminobenzyl)-6-(3-ethoxy-4-methoxyphenyl)-5-ethyl-2,3,4,5-tetrahydropyridazin-3-one;
with hexanoyl chloride:
  2-(4-hexanoylaminobenzyl)-6-(3-ethoxy-4-methoxyphenyl)-5-ethyl-2,3,4,5-tetrahydropyridazin-3-one;
with pentafluoropropionyl chloride:
  2-(4-pentafluoropropionylaminobenzyl)-6-(3-ethoxy-4-methoxyphenyl)-5-ethyl-2,3,4,5-tetrahydropyridazin-3-one.

The following are obtained analogously by reaction of 2-(4-aminobenzyl)-6-(3-cyclopentyloxy-4-methoxyphenyl)-5-ethyl-2,3,4,5-tetrahydropyridazin-3-one
with acetyl chloride:
  2-(4-acetamidobenzyl)-6-(3-cyclopentyloxy-4-methoxyphenyl)-5-ethyl-2,3,4,5-tetrahydropyridazin-3-one;
with trifluoroacetyl chloride:
  2-(4-trifluoroacetamidobenzyl)-6-(3-cyclopentyloxy-4-methoxyphenyl)-5-ethyl-2,3,4,5-tetrahydropyridazin-3-one, m.p. 162°;
with methylsulfonyl chloride:
  2-(4-methylsulfonamidobenzyl)-6-(3-cyclopentyloxy-4-methoxyphenyl)-5-ethyl-2,3,4,5-tetrahydropyridazin-3-one;
with propionyl chloride:
  2-(4-propionylaminobenzyl)-6-(3-cyclopentyloxy-4-methoxyphenyl)-5-ethyl-2,3,4,5-tetrahydropyridazin-3-one, m.p. 69°;

with 2,2-dimethylpropionyl chloride:
  2-(4-tert-butylcarbonylaminobenzyl)-6-(3-cyclopentyloxy-4-methoxyphenyl)-5-ethyl-2,3,4,5-tetrahydropyridazin-3-one;
with butyryl chloride:
  2-(4-butyrylaminobenzyl)-6-(3-cyclopentyloxy-4-methoxyphenyl)-5-ethyl-2,3,4,5-tetrahydropyridazin-3-one;
with isobutyryl chloride:
  2-(4-isobutyrylaminobenzyl)-6-(3-cyclopentyloxy-4-methoxyphenyl)-5-ethyl-2,3,4,5-tetrahydropyridazin-3-one;
with methyl chloroformate:
  2-(4-methoxycarbonylaminobenzyl)-6-(3-cyclopentyloxy-4-methoxyphenyl)-5-ethyl-2,3,4,5-tetrahydropyridazin-3-one;
with pivalyl chloride:
  2-(4-pivalylaminobenzyl)-6-(3-cyclopentyloxy-4-methoxyphenyl)-5-ethyl-2,3,4,5-tetrahydropyridazin-3-one;
with cyclopentanecarbonyl chloride:
  2-(4-cyclopentylcarbamoylbenzyl)-6-(3-cyclopentyloxy-4-methoxyphenyl)-5-ethyl-2,3,4,5-tetrahydropyridazin-3-one;
with ethyl chloroformate:
  2-(4-ethoxycarbonylaminobenzyl)-6-(3-cyclopentyloxy-4-methoxyphenyl)-5-ethyl-2,3,4,5-tetrahydropyridazin-3-one, m.p. 73°
with methoxalyl chloride:
  2-(4-methoxalylaminobenzyl)-6-(3-cyclopentyloxy-4-methoxyphenyl)-5-ethyl-2,3,4,5-tetrahydropyridazin-3-one;
with chloroformamide:
  2-(4-ureidobenzyl)-6-(3-cyclopentyloxy-4-methoxyphenyl)-5-ethyl-2,3,4,5-tetrahydropyridazin-3-one;
with pentanoyl chloride:
  2-(4-pentanoylaminobenzyl)-6-(3-cyclopentyloxy-4-methoxyphenyl)-5-ethyl-2,3,4,5-tetrahydropyridazin-3-one;
with hexanoyl chloride:
  2-(4-hexanoylaminobenzyl)-6-(3-cyclopentyloxy-4-methoxyphenyl)-5-ethyl-2,3,4,5-tetrahydropyridazin-3-one;
with pentafluoropropionyl chloride:
  2-(4-pentafluoropropionylaminobenzyl)-6-(3-cyclopentyloxy-4-methoxyphenyl)-5-ethyl-2,3,4,5-tetrahydropyridazin-3-one.

The following are obtained analogously by reaction of 2-(4-aminophenethyl)-6-(3,4-dimethoxyphenyl)-5-ethyl-2,3,4,5-tetrahydropyridazin-3-one
with acetyl chloride:
  2-(4-acetamidophenethyl)-6-(3,4-dimethoxyphenyl)-5-ethyl-2,3,4,5-tetrahydropyridazin-3-one;
with trifluoroacetyl chloride:
  2-(4-trifluoroacetamidophenethyl)-6-(3,4-dimethoxyphenyl)-5-ethyl-2,3,4,5-tetrahydropyridazin-3-one;
with methylsulfonyl chloride:
  2-(4-methylsulfonamidophenethyl)-6-(3,4-dimethoxyphenyl)-5-ethyl-2,3,4,5-tetrahydropyridazin-3-one;
with propionyl chloride:
  2-(4-propionylaminophenethyl)-6-(3,4-dimethoxyphenyl)-5-ethyl-2,3,4,5-tetrahydropyridazin-3-one;
with butyryl chloride:
  2-(4-butyrylaminophenethyl)-6-(3,4-dimethoxyphenyl)-5-ethyl-2,3,4,5-tetrahydropyridazin-3-one;
with isobutyryl chloride:
  2-(4-isobutyrylaminophenethyl)-6-(3,4-dimethoxyphenyl)-5-ethyl-2,3,4,5-tetrahydropyridazin-3-one;
with methyl chloroformate:
  2-(4-methoxycarbonylaminophenethyl)-6-(3,4-dimethoxyphenyl)-5-ethyl-2, 3,4,5-tetrahydropyridazin-3-one;
with pivalyl chloride:
  2-(4-pivalylaminophenethyl)-6-(3,4-dimethoxyphenyl)-5-ethyl-2,3,4,5-tetrahydropyridazin-3-one;
with cyclopentanecarbonyl chloride:
  2-(4-cyclopentylcarbamoylphenethyl)-6-(3,4-dimethoxyphenyl)-5-ethyl-2,3,4,5-tetrahydropyridazin-3-one;
with ethyl chloroformate:
  2-(4-ethoxycarbonylaminophenethyl)-6-(3,4-dimethoxyphenyl)-5-ethyl-2,3,4,5-tetrahydropyridazin-3-one;
with methoxalyl chloride:
  2-(4-methoxalylaminophenethyl)-6-(3,4-dimethoxyphenyl)-5-ethyl-2,3,4,5-tetrahydropyridazin-3-one;
with chloroformamide:
  2-(4-ureidophenethyl)-6-(3,4-dimethoxyphenyl)-5-ethyl-2,3,4,5-tetrahydropyridazin-3-one;
with pentanoyl chloride:
  2-(4-pentanoylaminophenethyl)-6-(3,4-dimethoxyphenyl)-5-ethyl-2,3,4,5-tetrahydropyridazin-3-one;
with hexanoyl chloride:
  2-(4-hexanoylaminophenethyl)-6-(3,4-dimethoxyphenyl)-5-ethyl-2,3,4,5-tetrahydropyridazin-3-one;
with pentafluoropropionyl chloride:
  2-(4-pentafluoropropionylaminophenethyl)-6-(3,4-dimethoxyphenyl)-5-ethyl-2,3,4,5-tetrahydropyridazin-3-one.

The following are obtained analogously by reaction of 2-(3-aminobenzyl)-6-(3,4-dimethoxyphenyl)-5-ethyl-2,3,4,5-tetrahydropyridazin-3-one
with acetyl chloride:
  2-(3-acetamidobenzyl)-6-(3,4-dimethoxyphenyl)-5-ethyl-2,3,4,5-tetrahydropyridazin-3-one;
with trifluoroacetyl chloride:
  2-(3-trifluoroacetamidobenzyl)-6-(3,4-dimethoxyphenyl)-5-ethyl-2,3,4,5-tetrahydropyridazin-3-one, m.p. 142°;
with methylsulfonyl chloride:
  2-(3-methylsulfonamidobenzyl)-6-(3,4-dimethoxyphenyl)-5-ethyl-2,3,4,5-tetrahydropyridazin-3-one;
with propionyl chloride:
  2-(3-propionylaminobenzyl)-6-(3,4-dimethoxyphenyl)-5-ethyl-2,3,4,5-tetrahydropyridazin-3-one, m.p. 126°;
with butyryl chloride:
  2-(3-butyrylaminobenzyl)-6-(3,4-dimethoxyphenyl)-5-ethyl-2,3,4,5-tetrahydropyridazin-3-one;
with isobutyryl chloride:
  2-(3-isobutyrylaminobenzyl)-6-(3,4-dimethoxyphenyl)-5-ethyl-2,3,4,5-tetrahydropyridazin-3-one;

with methyl chloroformate:
   2-(3-methoxycarbonylaminobenzyl)-6-(3,4-dimethoxyphenyl)-5-ethyl-2,3,4,5-tetrahydropyridazin-3-one;
with pivalyl chloride:
   2-(3-pivalylaminobenzyl)-6-(3,4-dimethoxyphenyl)-5-ethyl-2,3,4,5-tetrahydropyridazin-3-one;
with cyclopentane carbonyl chloride:
   2-(3-cyclopentylcarbamoylbenzyl)-6-(3,4-dimethoxyphenyl)-5-ethyl-2,3,4,5-tetrahydropyridazin-3-one;
with ethyl chloroformate:
   2-(3-ethoxycarbonylaminobenzyl)-6-(3,4-dimethoxyphenyl)-5-ethyl-2,3,4,5-tetrahydropyridazin-3-one, m.p. 54°;
with methoxalyl chloride:
   2-(3-methoxalylaminobenzyl)-6-(3,4-dimethoxyphenyl)-5-ethyl-2,3,4,5-tetrahydropyridazin-3-one;
with chloroformamide:
   2-(3-ureidobenzyl)-6-(3,4-dimethoxyphenyl)-5-ethyl-2,3,4,5-tetrahydropyridazin-3-one;
with pentanoyl chloride:
   2-(3-pentanoylaminobenzyl)-6-(3,4-dimethoxyphenyl)-5-ethyl-2,3,4,5-tetrahydropyridazin-3-one;
with hexanoyl chloride:
   2-(3-hexanoylaminobenzyl)-6-(3,4-dimethoxyphenyl)-5-ethyl-2,3,4,5-tetrahydropyridazin-3-one;
with pentafluoropropionyl chloride:
   2-(3-pentafluoropropionylaminobenzyl)-6-(3,4-dimethoxyphenyl)-5-ethyl-2,3,4,5-tetrahydropyridazin-3-one.

The following are obtained analogously by reaction of 2-(4-aminobenzyl)-6-(3-fluoromethoxy-4-methoxyphenyl)-5-ethyl-2,3,4,5-tetrahydropyridazin-3-one
with acetyl chloride:
   2-(4-acetamidobenzyl)-6-(3-fluoromethoxy-4-methoxyphenyl)-5-ethyl-2,3,4,5-tetrahydropyridazin-3-one;
with trifluoroacetyl chloride:
   2-(4-trifluoroacetamidobenzyl)-6-(3-fluoromethoxy-4-methoxyphenyl)-5-ethyl-2,3,4,5-tetrahydropyridazin-3-one;
with methylsulfonyl chloride:
   2-(4-methylsulfonamidobenzyl)-6-(3-fluoromethoxy-4-methoxyphenyl)-5-ethyl-2,3,4,5-tetrahydropyridazin-3-one;
with propionyl chloride:
   2-(4-propionylaminobenzyl)-6-(3-fluoromethoxy-4-methoxyphenyl)-5-ethyl-2,3,4,5-tetrahydropyridazin-3-one;
with butyryl chloride:
   2-(4-butyrylaminobenzyl)-6-(3-fluoromethoxy-4-methoxyphenyl)-5-ethyl-2,3,4,5-tetrahydropyridazin-3-one;
with isobutyryl chloride:
   2-(4-isobutyrylaminobenzyl)-6-(3-fluoromethoxy-4-methoxyphenyl)-5-ethyl-2,3,4,5-tetrahydropyridazin-3-one;
with methyl chloroformate:
   2-(4-methoxycarbonylaminobenzyl)-6-(3-fluoromethoxy-4-methoxyphenyl)-5-ethyl-2,3,4,5-tetrahydropyridazin-3-one;
with pivalyl chloride:
   2-(4-pivalylaminobenzyl)-6-(3-fluoromethoxy-4-methoxyphenyl)-5-ethyl-2,3,4,5-tetrahydropyridazin-3-one;
with cyclopentanecarbonyl chloride:
   2-(4-cyclopentylcarbamoylbenzyl)-6-(3-fluoromethoxy-4-methoxyphenyl)-5-ethyl-2,3,4,5-tetrahydropyridazin-3-one;
with ethyl chloroformate:
   2-(4-ethoxycarbonylaminobenzyl)-6-(3-fluoromethoxy-4-methoxyphenyl)-5-ethyl-2,3,4,5-tetrahydropyridazin-3-one;
with methoxalyl chloride:
   2-(4-methoxalylaminobenzyl)-6-(3-fluoromethoxy-4-methoxyphenyl)-5-ethyl-2,3,4,5-tetrahydropyridazin-3-one;
with chloroformamide:
   2-(4-ureidobenzyl)-6-(3-fluoromethoxy-4-methoxyphenyl)-5-ethyl-2,3,4,5-tetrahydropyridazin-3-one;
with pentanoyl chloride:
   2-(4-pentanoylaminobenzyl)-6-(3-fluoromethoxy-4-methoxyphenyl)-5-ethyl-2,3,4,5-tetrahydropyridazin-3-one;
with hexanoyl chloride:
   2-(4-hexanoylaminobenzyl)-6-(3-fluoromethoxy-4-methoxyphenyl)-5-ethyl-2,3,4,5-tetrahydropyridazin-3-one;
with pentafluoropropionyl chloride:
   2-(4-pentafluoropropionylaminobenzyl)-6-(3-fluoromethoxy-4-methoxyphenyl)-5-ethyl-2,3,4,5-tetrahydropyridazin-3-one.

The following are obtained analogously by reaction of 2-(4-aminobenzyl)-6-(3-difluoromethoxy-4-methoxyphenyl)-5-ethyl-2,3,4,5-tetrahydropyridazin-3-one
with acetyl chloride:
   2-(4-acetamidobenzyl)-6-(3-difluoromethoxy-4-methoxyphenyl)-5-ethyl-2,3,4,5-tetrahydropyridazin-3-one;
with trifluoroacetyl chloride:
   2-(4-trifluoroacetamidobenzyl)-6-(3-difluoromethoxy-4-methoxyphenyl)-5-ethyl-2,3,4,5-tetrahydropyridazin-3-one;
with methylsulfonyl chloride:
   2-(4-methylsulfonamidobenzyl)-6-(3-difluoromethoxy-4-methoxyphenyl)-5-ethyl-2,3,4,5-tetrahydropyridazin-3-one;
with propionyl chloride:
   2-(4-propionylaminobenzyl)-6-(3-difluoromethoxy-4-methoxyphenyl)-5-ethyl-2,3,4,5-tetrahydropyridazin-3-one;
with butyryl chloride:
   2-(4-butyrylaminobenzyl)-6-(3-difluoromethoxy-4-methoxyphenyl)-5-ethyl-2,3,4,5-tetrahydropyridazin-3-one;
with isobutyryl chloride:
   2-(4-isobutyrylaminobenzyl)-6-(3-difluoromethoxy-4-methoxyphenyl)-5-ethyl-2,3,4,5-tetrahydropyridazin-3-one;
with methyl chloroformate:
   2-(4-methoxycarbonylaminobenzyl)-6-(3-difluoromethoxy-4-methoxyphenyl)-5-ethyl-2,3,4,5-tetrahydropyridazin-3-one;
with pivalyl chloride:
   2-(4-pivalylaminobenzyl)-6-(3-difluoromethoxy-4-methoxyphenyl)-5-ethyl-2,3,4,5-tetrahydropyridazin-3-one;

with cyclopentanecarbonyl chloride:
  2-(4-cyclopentylcarbamoylbenzyl)-6-(3-difluoromethoxy-4-methoxyphenyl)-5-ethyl-2,3,4,5-tetrahydropyridazin-3-one;
with ethyl chloroformate:
  2-(4-ethoxycarbonylaminobenzyl)-6-(3-difluoromethoxy-4-methoxyphenyl)-5-ethyl-2,3,4,5-tetrahydropyridazin-3-one;
with methoxalyl chloride:
  2-(4-methoxalylaminobenzyl)-6-(3-difluoromethoxy-4-methoxyphenyl)-5-ethyl-2,3,4,5-tetrahydropyridazin-3-one;
with chloroformamide:
  2-(4-ureidobenzyl)-6-(3-difluoromethoxy-4-methoxyphenyl)-5-ethyl-2, 3, 4, 5-tetrahydropyridazin-3-one;
with pentanoyl chloride:
  2-(4-pentanoylaminobenzyl)-6-(3-difluoromethoxy-4-methoxyphenyl)-5-ethyl-2,3,4,5-tetrahydropyridazin-3-one;
with hexanoyl chloride:
  2-(4-hexanoylaminobenzyl)-6-(3-difluoromethoxy-4-methoxyphenyl)-5-ethyl-2,3,4,5-tetrahydropyridazin-3-one;
with pentafluoropropionyl chloride:
  2-(4-pentafluoropropionylaminobenzyl)-6-(3-difluoromethoxy-4-methoxyphenyl)-5-ethyl-2,3,4,5-tetrahydropyridazin-3-one.

The following are obtained analogously by reaction of 2-(4-aminobenzyl)-6-(3-trifluoromethoxy-4-methoxyphenyl)-5-ethyl-2,3,4,5-tetrahydropyridazin-3-one
with acetyl chloride:
  2-(4-acetamidobenzyl)-6-(3-trifluoromethoxy-4-methoxyphenyl)-5-ethyl-2,3,4,5-tetrahydropyridazin-3-one;
with trifluoroacetyl chloride:
  2-(4-trifluoroacetamidobenzyl)-6-(3-trifluoromethoxy-4-methoxyphenyl)-5-ethyl-2,3,4,5-tetrahydropyridazin-3-one;
with methylsulfonyl chloride:
  2-(4-methylsulfonamidobenzyl)-6-(3-trifluoromethoxy-4-methoxyphenyl)-5-ethyl-2,3,4,5-tetrahydropyridazin-3-one;
with propionyl chloride:
  2-(4-propionylaminobenzyl)-6-(3-trifluoromethoxy-4-methoxyphenyl)-5-ethyl-2,3,4,5-tetrahydropyridazin-3-one;
with butyryl chloride:
  2-(4-butyrylaminobenzyl)-6-(3-trifluoromethoxy-4-methoxyphenyl)-5-ethyl-2,3,4,5-tetrahydropyridazin-3-one;
with isobutyryl chloride:
  2-(4-isobutyrylaminobenzyl)-6-(3-trifluoromethoxy-4-methoxyphenyl)-5-ethyl-2,3,4,5-tetrahydropyridazin-3-one;
with methyl chloroformate:
  2-(4-methoxycarbonylaminobenzyl)-6-(3-trifluoromethoxy-4-methoxyphenyl)-5-ethyl-2,3,4,5-tetrahydropyridazin-3-one;
with pivalyl chloride:
  2-(4-pivalylaminobenzyl)-6-(3-trifluoromethoxy-4-methoxyphenyl)-5-ethyl-2,3,4,5-tetrahydropyridazin-3-one;
with cyclopentanecarbonyl chloride:
  2-(4-cyclopentylcarbamoylbenzyl)-6-(3-trifluoromethoxy-4-methoxyphenyl)-5-ethyl-2,3,4,5-tetrahydropyridazin-3-one;
with ethyl chloroformate:
  2-(4-ethoxycarbonylaminobenzyl)-6-(3-trifluoromethoxy-4-methoxyphenyl)-5-ethyl-2,3,4,5-tetrahydropyridazin-3-one;
with methoxalyl chloride:
  2-(4-methoxalylaminobenzyl)-6-(3-trifluoromethoxy-4-methoxyphenyl)-5-ethyl-2,3,4,5-tetrahydropyridazin-3-one;
with chloroformamide:
  2-(4-ureidobenzyl)-6-(3-trifluoromethoxy-4-methoxyphenyl)-5-ethyl-2,3,4,5-tetrahydropyridazin-3-one;
with pentanoyl chloride:
  2-(4-pentanoylaminobenzyl)-6-(3-trifluoromethoxy-4-methoxyphenyl)-5-ethyl-2,3,4,5-tetrahydropyridazin-3-one;
with hexanoyl chloride:
  2-(4-hexanoylaminobenzyl)-6-(3-trifluoromethoxy-4-methoxyphenyl)-5-ethyl-2,3,4,5-tetrahydropyridazin-3-one;
with pentafluoropropionyl chloride:
  2-(4-pentafluoropropionylaminobenzyl)-6-(3-trifluoromethoxy-4-methoxyphenyl)-5-ethyl-2,3,4,5-tetrahydropyridazin-3-one.

The following are obtained analogously by reaction of 2-(4-aminobenzyl)-6-(3-methoxy-4-fluoromethoxyphenyl)-5-ethyl-2,3,4,5-tetrahydropyridazin-3-one
with acetyl chloride:
  2-(4-acetamidobenzyl)-6-(3-methoxy-4-fluoromethoxyphenyl)-5-ethyl-2,3,4,5-tetrahydropyridazin-3-one;
with trifluoroacetyl chloride:
  2-(4-trifluoroacetamidobenzyl)-6-(3-methoxy-4-fluoromethoxyphenyl)-5-ethyl-2,3,4,5-tetrahydropyridazin-3-one;
with methylsulfonyl chloride:
  2-(4-methylsulfonamidobenzyl)-6-(3-methoxy-4-fluoromethoxyphenyl)-5-ethyl-2,3,4,5-tetrahydropyridazin-3-one;
with propionyl chloride:
  2-(4-propionylaminobenzyl)-6-(3-methoxy-4-fluoromethoxyphenyl)-5-ethyl-2,3,4,5-tetrahydropyridazin-3-one;
with butyryl chloride:
  2-(4-butyrylaminobenzyl)-6-(3-methoxy-4-fluoromethoxyphenyl)-5-ethyl-2,3,4,5-tetrahydropyridazin-3-one;
with isobutyryl chloride:
  2-(4-isobutyrylaminobenzyl)-6-(3-methoxy-4-fluoromethoxyphenyl)-5-ethyl-2,3,4,5-tetrahydropyridazin-3-one;
with methyl chloroformate:
  2-(4-methoxycarbonylaminobenzyl)-6-(3-methoxy4-fluoromethoxyphenyl)-5-ethyl-2,3,4,5-tetrahydropyridazin-3-one;
with pivalyl chloride:
  2-(4-pivalylaminobenzyl)-6-(3-methoxy-4-fluoromethoxyphenyl)-5-ethyl-2,3,4,5-tetrahydropyridazin-3-one;

with cyclopentanecarbonyl chloride:
   2-(4-cyclopentylcarbamoylbenzyl)-6-(3-methoxy-4-fluoromethoxyphenyl)-5-ethyl-2,3,4,5-tetrahydropyridazin-3-one;
with ethyl chloroformate:
   2-(4-ethoxycarbonylaminobenzyl)-6-(3-methoxy-4-fluoromethoxyphenyl)-5-ethyl-2,3,4,5-tetrahydropyridazin-3-one;
with methoxalyl chloride:
   2-(4-methoxalylaminobenzyl)-6-(3-methoxy-4-fluoromethoxyphenyl)-5-ethyl-2,3,4,5-tetrahydropyridazin-3-one;
with chloroformamide:
   2-(4-ureidobenzyl)-6-(3-methoxy-4-fluoromethoxyphenyl)-5-ethyl-2,3,4,5-tetrahydropyridazin-3-one;
with pentanoyl chloride:
   2-(4-pentanoylaminobenzyl)-6-(3-methoxy-4-fluoromethoxyphenyl)-5-ethyl-2,3,4,5-tetrahydropyridazin-3-one;
with hexanoyl chloride:
   2-(4-hexanoylaminobenzyl)-6-(3-methoxy-4-fluoromethoxyphenyl)-5-ethyl-2,3,4,5-tetrahydropyridazin-3-one;
with pentafluoropropionyl chloride:
   2-(4-pentafluoropropionylaminobenzyl)-6-(3-methoxy-4-fluoromethoxyphenyl)-5-ethyl-2,3,4,5-tetrahydropyridazin-3-one.

The following are obtained analogously by reaction of 2-(4-aminobenzyl)-6-(3-methoxy-4-difluoromethoxyphenyl)-5-ethyl-2,3,4,5-tetrahydropyridazin-3-one
with acetyl chloride:
   2-(4-acetamidobenzyl)-6-(3-methoxy-4-difluoromethoxyphenyl)-5-ethyl-2,3,4,5-tetrahydropyridazin-3-one;
with trifluoroacetyl chloride:
   2-(4-trifluoroacetamidobenzyl)-6-(3-methoxy-4-difluoromethoxyphenyl)-5-ethyl-2,3,4,5-tetrahydropyridazin-3-one;
with methylsulfonyl chloride:
   2-(4-methylsulfonamidobenzyl)-6-(3-methoxy-4-difluoromethoxyphenyl)-5-ethyl-2,3,4,5-tetrahydropyridazin-3-one;
with propionyl chloride:
   2-(4-propionylaminobenzyl)-6-(3-methoxy-4-difluoromethoxyphenyl)-5-ethyl-2,3,4,5-tetrahydropyridazin-3-one;
with butyryl chloride:
   2-(4-butyrylaminobenzyl)-6-(3-methoxy-4-difluoromethoxyphenyl)-5-ethyl-2,3,4,5-tetrahydropyridazin-3-one;
with isobutyryl chloride:
   2-(4-isobutyrylaminobenzyl)-6-(3-methoxy-4-difluoromethoxyphenyl)-5-ethyl-2,3,4,5-tetrahydropyridazin-3-one;
with methyl chloroformate:
   2-(4-methoxycarbonylaminobenzyl)-6-(3-methoxy-4-difluoromethoxyphenyl)-5-ethyl-2,3,4,5-tetrahydropyridazin-3-one;
with pivalyl chloride:
   2-(4-pivalylaminobenzyl)-6-(3-methoxy-4-difluoromethoxyphenyl)-5-ethyl-2,3,4,5-tetrahydropyridazin-3-one;
with cyclopentanecarbonyl chloride:
   2-(4-cyclopentylcarbamoylbenzyl)-6-(3-methoxy-4-difluoromethoxyphenyl)-5-ethyl-2,3,4,5-tetrahydropyridazin-3-one;
with ethyl chloroformate:
   2-(4-ethoxycarbonylaminobenzyl)-6-(3-methoxy-4-difluoromethoxyphenyl)-5-ethyl-2,3,4,5-tetrahydropyridazin-3-one;
with methoxalyl chloride:
   2-(4-methoxalylaminobenzyl)-6-(3-methoxy-4-difluoromethoxyphenyl)-5-ethyl-2,3,4,5-tetrahydropyridazin-3-one;
with chloroformamide:
   2-(4-ureidobenzyl)-6-(3-methoxy-4-difluoromethoxyphenyl)-5-ethyl-2,3,4,5-tetrahydropyridazin-3-one;
with pentanoyl chloride:
   2-(4-pentanoylaminobenzyl)-6-(3-methoxy-4-difluoromethoxyphenyl)-5-ethyl-2,3,4,5-tetrahydropyridazin-3-one;
with hexanoyl chloride:
   2-(4-hexanoylaminobenzyl)-6-(3-methoxy-4-difluoromethoxyphenyl)-5-ethyl-2,3,4,5-tetrahydropyridazin-3-one;
with pentafluoropropionyl chloride:
   2-(4-pentafluoropropionylaminobenzyl)-6-(3-methoxy-4-difluoromethoxyphenyl)-5-ethyl-2,3,4,5-tetrahydropyridazin-3-one.

The following are obtained analogously by reaction of 2-(4-aminobenzyl)-6-(3-methoxy-4-trifluoromethoxyphenyl)-5-ethyl-2,3,4,5-tetrahydropyridazin-3-one
with acetyl chloride:
   2-(4-acetamidobenzyl)-6-(3-methoxy-4-trifluoromethoxyphenyl)-5-ethyl-2,3,4,5-tetrahydropyridazin-3-one;
with trifluoroacetyl chloride:
   2-(4-trifluoroacetamidobenzyl)-6-(3-methoxy-4-trifluoromethoxyphenyl)-5-ethyl-2,3,4,5-tetrahydropyridazin-3-one;
with methylsulfonyl chloride:
   2-(4-methylsulfonamidobenzyl)-6-(3-methoxy-4-trifluoromethoxyphenyl)-5-ethyl-2,3,4,5-tetrahydropyridazin-3-one;
with propionyl chloride:
   2-(4-propionylaminobenzyl)-6-(3-methoxy-4-trifluoromethoxyphenyl)-5-ethyl-2,3,4,5-tetrahydropyridazin-3-one;
with butyryl chloride:
   2-(4-butyrylaminobenzyl)-6-(3-methoxy-4-trifluoromethoxyphenyl)-5-ethyl-2,3,4,5-tetrahydropyridazin-3-one;
with isobutyryl chloride:
   2-(4-isobutyrylaminobenzyl)-6-(3-methoxy-4-trifluoromethoxyphenyl)-5-ethyl-2,3,4,5-tetrahydropyridazin-3-one;
with methyl chloroformate:
   2-(4-methoxycarbonylaminobenzyl)-6-(3-methoxy-4-trifluoromethoxyphenyl)-5-ethyl-2,3,4,5-tetrahydropyridazin-3-one;
with pivalyl chloride:
   2-(4-pivalylaminobenzyl)-6-(3-methoxy-4-trifluoromethoxyphenyl)-5-ethyl-2,3,4,5-tetrahydropyridazin-3-one;
with cyclopentanecarbonyl chloride:
   2-(4-cyclopentylcarbamoylbenzyl)-6-(3-methoxy-4-trifluoromethoxyphenyl)-5-ethyl-2,3,4,5-tetrahydropyridazin-3-one;

with ethyl chloroformate:
   2-(4-ethoxycarbonylaminobenzyl)-6-(3-methoxy-4-trifluoromethoxyphenyl)-5-ethyl-2,3,4,5-tetrahydropyridazin-3-one;
with methoxalyl chloride:
   2-(4-methoxalylaminobenzyl)-6-(3-methoxy-4-trifluoromethoxyphenyl)-5-ethyl-2,3,4,5-tetrahydropyridazin-3-one;
with chloroformamide:
   2-(4-ureidobenzyl)-6-(3-methoxy-4-trifluoromethoxyphenyl)-5-ethyl-2,3,4,5-tetrahydropyridazin-3-one;
with pentanoyl chloride:
   2-(4-pentanoylaminobenzyl)-6-(3-methoxy-4-trifluoromethoxyphenyl)-5-ethyl-2,3,4,5-tetrahydropyridazin-3-one;
with hexanoyl chloride:
   2-(4-hexanoylaminobenzyl)-6-(3-methoxy-4-trifluoromethoxyphenyl)-5-ethyl-2,3,4,5-tetrahydropyridazin-3-one;
with pentafluoropropionyl chloride:
   2-(4-pentafluoropropionylaminobenzyl)-6-(3-methoxy-4-trifluoromethoxyphenyl)-5-ethyl-2,3,4,5-tetrahydropyridazin-3-one.

The following are obtained analogously by reaction of 2-(4-aminobenzyl)-6-(3-ethoxy-4-methoxyphenyl)-2,3,4,5-tetrahydropyridazin-3-one, m.p. 120°
with acetyl chloride:
   2-(4-acetamidobenzyl)-6-(3-ethoxy-4-methoxyphenyl)-2,3,4,5-tetrahydropyridazin-3-one, m.p. 170°;
with trifluoroacetyl chloride:
   2-(4-trifluoroacetamidobenzyl)-6-(3-ethoxy-4-methoxyphenyl)-2,3,4,5-tetrahydropyridazin-3-one;
with methylsulfonyl chloride:
   2-(4-methylsulfonamidobenzyl)-6-(3-ethoxy-4-methoxyphenyl)-2,3,4,5-tetrahydropyridazin-3-one;
with propionyl chloride:
   2-(4-propionylaminobenzyl)-6-(3-ethoxy-4-methoxyphenyl)-2,3,4,5-tetrahydropyridazin-3-one;
with butyryl chloride:
   2-(4-butyrylaminobenzyl)-6-(3-ethoxy-4-methoxyphenyl)-2,3,4,5-tetrahydropyridazin-3-one;
with isobutyryl chloride:
   2-(4-isobutyrylaminobenzyl)-6-(3-ethoxy-4-methoxyphenyl)-2,3,4,5-tetrahydropyridazin-3-one;
with methyl chloroformate:
   2-(4-methoxycarbonylaminobenzyl)-6-(3-ethoxy-4-methoxyphenyl)-2,3,4,5-tetrahydropyridazin-3-one;
with pivalyl chloride:
   2-(4-pivalylaminobenzyl)-6-(3-ethoxy-4-methoxyphenyl)-2,3,4,5-tetrahydropyridazin-3-one;
with cyclopentanecarbonyl chloride:
   2-(4-cyclopentylcarbamoylbenzyl)-6-(3-ethoxy-4-methoxyphenyl)-2,3,4,5-tetrahydropyridazin-3-one;
with ethyl chloroformate:
   2-(4-ethoxycarbonylaminobenzyl)-6-(3-ethoxy-4-methoxyphenyl)-2,3,4,5-tetrahydropyridazin-3-one, m.p. 128°;
with methoxalyl chloride:
   2-(4-methoxalylaminobenzyl)-6-(3-ethoxy-4-methoxyphenyl)-2,3,4,5-tetrahydropyridazin-3-one;
with chloroformamide:
   2-(4-ureidobenzyl)-6-(3-ethoxy-4-methoxyphenyl)-2,3,4,5-tetrahydropyridazin-3-one;
with pentanoyl chloride:
   2-(4-pentanoylaminobenzyl)-6-(3-ethoxy-4-methoxyphenyl)-2,3,4,5-tetrahydropyridazin-3-one;
with hexanoyl chloride:
   2-(4-hexanoylaminobenzyl)-6-(3-ethoxy-4-methoxyphenyl)-2,3,4,5-tetrahydropyridazin-3-one;
with pentafluoropropionyl chloride:
   2-(4-pentafluoropropionylaminobenzyl)-6-(3-ethoxy-4-methoxyphenyl)-2,3,4,5-tetrahydropyridazin-3-one.

The following are obtained analogously by reaction of 2-(4-aminobenzyl)-6-(3-cyclopentyloxy-4-methoxyphenyl)-2,3,4,5-tetrahydropyridazin-3-one
with acetyl chloride:
   2-(4-acetamidobenzyl)-6-(3-cyclopentyloxy-4-methoxyphenyl)-2,3,4,5-tetrahydropyridazin-3-one;
with trifluoroacetyl chloride:
   2-(4-trifluoroacetamidobenzyl)-6-(3-cyclopentyloxy-4-methoxyphenyl)-2,3,4,5-tetrahydropyridazin-3-one;
with methylsulfonyl chloride:
   2-(4-methylsulfonamidobenzyl)-6-(3-cyclopentyloxy-4-methoxyphenyl)-2,3,4,5-tetrahydropyridazin-3-one;
with propionyl chloride:
   2-(4-propionylaminobenzyl)-6-(3-cyclopentyloxy-4-methoxyphenyl)-2,3,4,5-tetrahydropyridazin-3-one;
with 2,2-dimethylpropionyl chloride:
   2-(4-tert-butylcarbonylaminobenzyl)-6-(3-cyclopentyloxy-4-methoxyphenyl)-2,3,4,5-tetrahydropyridazin-3-one;
with butyryl chloride:
   2-(4-butyrylaminobenzyl)-6-(3-cyclopentyloxy-4-methoxyphenyl)-2,3,4,5-tetrahydropyridazin-3-one;
with isobutyryl chloride:
   2-(4-isobutyrylaminobenzyl)-6-(3-cyclopentyloxy-4-methoxyphenyl)-2,3,4,5-tetrahydropyridazin-3-one;
with methyl chloroformate:
   2-(4-methoxycarbonylaminobenzyl)-6-(3-cyclopentyloxy-4-methoxyphenyl)-2,3,4,5-tetrahydropyridazin-3-one;
with pivalyl chloride:
   2-(4-pivalylaminobenzyl)-6-(3-cyclopentyloxy-4-methoxyphenyl)-2,3,4,5-tetrahydropyridazin-3-one;
with cyclopentanecarbonyl chloride:
   2-(4-cyclopentylcarbamoylbenzyl)-6-(3-cyclopentyloxy-4-methoxyphenyl)-2,3,4,5-tetrahydropyridazin-3-one;
with ethyl chloroformate:
   2-(4-ethoxycarbonylaminobenzyl)-6-(3-cyclopentyloxy-4-methoxyphenyl)-2,3,4,5-tetrahydropyridazin-3-one;
with methoxalyl chloride:
   2-(4-methoxalylaminobenzyl)-6-(3-cyclopentyloxy-4-methoxyphenyl)-2,3,4,5-tetrahydropyridazin-3-one;
with chloroformamide:
   2-(4-ureidobenzyl)-6-(3-cyclopentyloxy-4-methoxyphenyl)-2,3,4,5-tetrahydropyridazin-3-one;
with pentanoyl chloride:
   2-(4-pentanoylaminobenzyl)-6-(3-cyclopentyloxy-4-methoxyphenyl)-2,3,4,5-tetrahydropyridazin-3-one;
with hexanoyl chloride:
   2-(4-hexanoylaminobenzyl)-6-(3-cyclopentyloxy-4-methoxyphenyl)-2,3,4,5-tetrahydropyridazin-3-one;
with pentafluoropropionyl chloride:
   2-(4-pentafluoropropionylaminobenzyl)-6-(3-cyclopentyloxy-4-methoxyphenyl)-2,3,4,5-tetrahydropyridazin-3-one.

The following are obtained analogously by reaction of 2-(4-aminophenethyl)-6-(3,4-dimethoxyphenyl)-2,3,4,5-tetrahydropyridazin-3-one with acetyl chloride:
  2-(4-acetamidophenethyl)-6-(3,4-dimethoxyphenyl)-2,3,4,5-tetrahydropyridazin-3-one;
with trifluoroacetyl chloride:
  2-(4-trifluoroacetamidophenethyl)-6-(3,4-dimethoxyphenyl)-2,3,4,5-tetrahydropyridazin-3-one;
with methylsulfonyl chloride:
  2-(4-methylsulfonamidophenethyl)-6-(3,4-dimethoxyphenyl)-2,3,4,5-tetrahydropyridazin-3-one;
with propionyl chloride:
  2-(4-propionylaminophenethyl)-6-(3,4-dimethoxyphenyl)-2,3,4,5-tetrahydropyridazin-3-one;
with butyryl chloride:
  2-(4-butyrylaminophenethyl)-6-(3,4-dimethoxyphenyl)-2,3,4,5-tetrahydropyridazin-3-one;
with isobutyryl chloride:
  2-(4-isobutyrylaminophenethyl)-6-(3,4-dimethoxyphenyl)-2,3,4,5-tetrahydropyridazin-3-one;
with methyl chloroformate:
  2-(4-methoxycarbonylaminophenethyl)-6-(3,4-dimethoxyphenyl)-2,3,4,5-tetrahydropyridazin-3-one;
with pivalyl chloride:
  2-(4-pivalylaminophenethyl)-6-(3,4-dimethoxyphenyl)2,3,4,5-tetrahydropyridazin-3-one;
with cyclopentanecarbonyl chloride:
  2-(4-cyclopentylcarbamoylphenethyl)-6-(3,4-dimethoxyphenyl)-2,3,4,5-tetrahydropyridazin-3-one;
with ethyl chloroformate:
  2-(4-ethoxycarbonylaminophenethyl)-6-(3,4-dimethoxyphenyl)-2,3,4,5-tetrahydropyridazin-3-one;
with methoxalyl chloride:
  2-(4-methoxalylaminophenethyl)-6-(3,4-dimethoxyphenyl)-2,3,4,5-tetrahydropyridazin-3-one;
with chloroformamide:
  2-(4-ureidophenethyl)-6-(3,4-dimethoxyphenyl)2,3,4,5-tetrahydropyridazin-3-one;
with pentanoyl chloride:
  2-(4-pentanoylaminophenethyl)-6-(3,4-dimethoxyphenyl)-2,3,4,5-tetrahydropyridazin-3-one;
with hexanoyl chloride:
  2-(4-hexanoylaminophenethyl)-6-(3,4-dimethoxyphenyl)-2,3,4,5-tetrahydropyridazin-3-one;
with pentafluoropropionyl chloride:
  2-(4-pentafluoropropionylaminophenethyl)-6-(3,4-dimethoxyphenyl)-2,3,4,5-tetrahydropyridazin-3-one.

The following are obtained analogously by reaction of 2-(3-aminobenzyl)-6-(3,4-dimethoxyphenyl)-2,3,4,5-tetrahydropyridazin-3-one
with acetyl chloride:
  2-(3-acetamidobenzyl)-6-(3,4-dimethoxyphenyl)-2,3,4,5-tetrahydropyridazin-2-one, m.p. 105°;
with trifluoroacetyl chloride:
  2-(3-trifluoroacetamidobenzyl)-6-(3,4-dimethoxyphenyl)-2,3,4,5-tetrahydropyridazin-3-one, m.p. 136°;
with methylsulfonyl chloride:
  2-(3-methylsulfonamidobenzyl)-6-(3,4-dimethoxyphenyl)-2,3,4,5-tetrahydropyridazin-3-one, m.p. 177°;
with propionyl chloride:
  2-(3-propionylaminobenzyl)-6-(3,4-dimethoxyphenyl)-2,3,4,5-tetrahydropyridazin-3-one, m.p. 152°;
with 2,2-dimethylpropionyl chloride:
  2-(3-tert-butylcarbonylaminobenzyl)-6-(3,4-dimethoxyphenyl)-2,3,4,5-tetrahydropyridazin-3-one;
with butyryl chloride:
  2-(3-butyrylaminobenzyl)-6-(3,4-dimethoxyphenyl)-2,3,4,5-tetrahydropyridazin-3-one;
with isobutyryl chloride:
  2-(3-isobutyrylaminobenzyl)-6-(3,4-dimethoxyphenyl)-2,3,4,5-tetrahydropyridazin-3-one;
with methyl chloroformate:
  2-(3-methoxycarbonylaminobenzyl)-6-(3,4-dimethoxyphenyl)-2,3,4,5-tetrahydropyridazin-3-one;
with pivalyl chloride:
  2-(3-pivalylaminobenzyl)-6-(3,4-dimethoxyphenyl)-2,3,4,5-tetrahydropyridazin-3-one;
with cyclopentanecarbonyl chloride:
  2-(3-cyclopentylcarbamoylbenzyl)-6-(3,4-dimethoxyphenyl)-2,3,4,5-tetrahydropyridazin-3-one;
with ethyl chlorofornmate:
  2-(3-ethoxycarbonylaminobenzyl)-6-(3,4-dimethoxyphenyl)-2,3,4,5-tetrahydropyridazin-3-one, m.p. 179°;
with methoxalyl chloride:
  2-(3-methoxalylaminobenzyl)-6-(3,4-dimethoxyphenyl)-2,3,4,5-tetrahydropyridazin-3-one;
with chloroformamide:
  2-(3-ureidobenzyl)-6-(3,4-dimethoxyphenyl)-2,3,4,5-tetrahydropyridazin-3-one;
with pentanoyl chloride:
  2-(3-pentanoylaminobenzyl)-6-(3,4-dimethoxyphenyl)-2,3,4,5-tetrahydropyridazin-3-one;
with hexanoyl chloride:
  2-(3-hexanoylaminobenzyl)-6-(3,4-dimethoxyphenyl)-2,3,4,5-tetrahydropyridazin-3-one;
with pentafluoropropionyl chloride:
  2-(3-pentafluoropropionylaminobenzyl)-6-(3,4-dimethoxyphenyl)-2,3,4,5-tetrahydropyridazin-3-one.

The following are obtained analogously by reaction of 2-(3-aminobenzyl)-6-(3-cyclopentyloxy-4-methoxyphenyl)-5-ethyl-2,3,4,5-tetrahydropyridazin-3-one
with acetyl chloride:
  2-(3-acetamidobenzyl)-6-(3-cyclopentyloxy-4-methoxyphenyl)-5-ethyl-2,3,4,5-tetrahydropyridazin-3-one;
with trifluoroacetyl chloride:
  2-(3-trifluoroacetamidobenzyl)-6-(3-cyclopentyloxy-4-methoxyphenyl)-5-ethyl-2,3,4,5-tetrahydropyridazin-3-one, m.p. 70°;
with methylsulfonyl chloride:
  2-(3-methylsulfonamidobenzyl)-6-(3-cyclopentyloxy-4-methoxyphenyl)-5-ethyl-2,3,4,5-tetrahydropyridazin-3-one;
with propionyl chloride:
  2-(3-propionylaminobenzyl)-6-(3-cyclopentyloxy-4-methoxyphenyl)-5-ethyl-2,3,4,5-tetrahydropyridazin-3-one, m.p. 113°;
with 2,2-dimethylpropionyl chloride:
  2-(3-tert-butylcarbonylaminobenzyl)-6-(3-cyclopentyloxy-4-methoxyphenyl)-5-ethyl-2,3,4,5-tetrahydropyridazin-3-one;
with butyryl chloride:
  2-(3-butyrylaminobenzyl)-6-(3-cyclopentyloxy-4-methoxyphenyl)-5-ethyl-2,3,4,5-tetrahydropyridazin-3-one;
with isobutyryl chloride:
  2-(3-isobutyrylaminobenzyl)-6-(3-cyclopentyloxy-4-methoxyphenyl)-5-ethyl-2,3,4,5-tetrahydropyridazin-3-one;

with methyl chloroformate:
2-(3-methoxycarbonylaminobenzyl)-6-(3-cyclopentyloxy-4-methoxyphenyl)-5-ethyl-2,3,4,5-tetrahydropyridazin-3-one;
with pivalyl chloride:
2-(3-pivalylaminobenzyl)-6-(3-cyclopentyloxy-4-methoxyphenyl)-5-ethyl-2,3,4,5-tetrahydropyridazin-3-one;
with cyclopentanecarbonyl chloride:
2-(3-cyclopentylcarbamoylbenzyl)-6-(3-cyclopentyloxy-4-methoxyphenyl)-5-ethyl-2,3,4,5-tetrahydropyridazin-3-one;
with ethyl chloroformate:
2-(3-ethoxycarbonylaminobenzyl)-6-(3-cyclopentyloxy-4-methoxyphenyl)-5-ethyl-2,3,4,5-tetrahydropyridazin-3-one, m.p. 153°;
with methoxalyl chloride:
2-(3-methoxalylaminobenzyl)-6-(3-cyclopentyloxy-4-methoxyphenyl)-5-ethyl-2,3,4,5-tetrahydropyridazin-3-one;
with chloroformamide:
2-(3-ureidobenzyl)-6-(3-cyclopentyloxy-4-methoxyphenyl)-5-ethyl-2,3,4,5-tetrahydropyridazin-3-one;
with pentanoyl chloride:
2-(3-pentanoylaminobenzyl)-6-(3-cyclopentyloxy-4-methoxyphenyl)-5-ethyl-2,3,4,5-tetrahydropyridazin-3-one;
with hexanoyl chloride:
2-(3-hexanoylaminobenzyl)-6-(3-cyclopentyloxy-4-methoxyphenyl)-5-ethyl-2,3,4,5-tetrahydropyridazin-3-one;
with pentafluoropropionyl chloride:
2-(3-pentafluoropropionylaminobenzyl)-6-(3-cyclopentyloxy-4-methoxyphenyl)-5-ethyl-2,3,4,5-tetrahydropyridazin-3-one.

Example 7

A solution of 2.4 g of 3-(3,4-dimethoxybenzoyl) propionic acid in 100 ml of glacial acetic acid is treated with 1.7 g of p-nitrobenzylhydrazine and stirred at 100° for 2 hours. The solvent is removed, the residue is worked up in the customary manner and 2-(4-nitrobenzyl)-6-(3,4-dimethoxyphenyl)-2,3,4,5-tetrahydropyridazin-3-one, m.p. 126°, is obtained.

The following is obtained analogously by reaction of 3-(3,4-dimethoxybenzoyl)propionic acid with 4-nitrophenylhydrazine 2-(4-nitrophenyl)-6-(3,4-dimethoxyphenyl)-2,3,4,5-tetrahydropyridazin-3-one.

The following examples relate to pharmaceutical preparations:

Example A: Injection Vials

A solution of 100 g of an active compound of the formula I and 5 g of disodium hydrogen phosphate is adjusted to pH 6.5 in 3 l of double-distilled water using 2N hydrochloric acid, sterile filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into molds and allowed to cool. Each suppository contains 20 mg of active compound.

Example C: Solution

A solution is prepared from 1 g of an active compound of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of double-distilled water. The mixture is adjusted to pH 6.8, made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in the customary manner to give tablets such that each tablet contains 10 mg of active compound.

Example F: Coated Tablets

Analogously to Example E, tablets are pressed which are then coated in a customary manner with a coating of sucrose, potato starch, talc, tragacanth and colorant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile filtered, filled into ampoules, lyophilized under sterile conditions and aseptically sealed. Each ampoule contains 10 mg of active compound.

What is claimed is:

1. A compound of the formula I

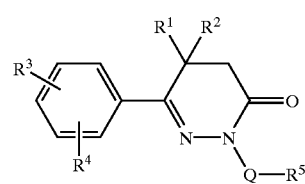

in which $R^1$ and $R^2$ in each case independently of one another are H or A, $R^3$ and $R^4$ in each case independently of one another are —OH, —$OR^{10}$, —S—$R^{10}$, —$SOR^{10}$, —$SO_2R^{10}$, Hal, —$NO_2$, —$NH_2$, —$NHR^{10}$ or —$NR^{10}R^{11}$, $R^5$ is a phenyl radical which is mono- or disubstituted by $R^6$ and/or $R^7$, Q is absent or is alkylene having 1–6 C atoms, $R^6$ and $R^7$ in each case independently of one another are —$NH_2$, —$NR^8R^9$, —$NHR^{10}$, —$NR^{10}R^{11}$, —$NO_2$, Hal, —CN, —COOH or —COOA, $R^8$ and $R^9$ in each case independently of one another are H, —COOA, —SO—A, —$SO_2A$, —$CONH_2$, —CONHA, —$CONA_2$, —CO—COOH, —CO—COOA, —CO—$CONH_2$, —CO—CONHA, —CO—

CONA$_2$, or acyl having 1–8 C atoms which is optionally substituted by 1–5 F and/or Cl atoms, A is alkyl having 1 to 6 C atoms which can be substituted by 1–5 F and/or Cl atoms, R$^{10}$ and R$^{11}$ both are A, cycloalkyl having 3–7 C atoms, methylenecycloalkyl having 4–8 C atoms or alkenyl having 2–8 C atoms and Hal is F, Cl, Br or I, and their physiologically acceptable salts.

2. An enantiomer of a compound of the formula I according to claim 1.

3. A compound of formula I of claim 1, which compound is a) 2-(4-Ethoxycarbonylaminobenzyl)-6-(3,4-dimethoxyphenyl)-2,3,4,5-tetrahydropyridazin-3-one;

b) 2-(3-methylsulfonamidobenzyl)-6-(3,4-dimethoxyphenyl)-2,3,4,5-tetrahydropyridazin-3-one;

c) 2-(3-acetamidobenzyl)-6-(3,4-dimethoxyphenyl)-2,3,4,5-tetrahydropyridazin-3-one;

d) 2-(4-trifluoracetamidobenzyl)-6-(3,4-dimethoxyphenyl)-5-ethyl-2,3,4,5-tetrahydropyridazin-3-one;

e) 2-(4-ethoxycarbonylaminobenzyl)-6-(3,4-dimethoxyphenyl)-5-ethyl-2,3,4,5-tetrahydropyridazin-3-one;

f) 2-(4-methoxycarbonylaminobenzyl)-6-(3,4-dimethoxyphenyl)-5-ethyl-2,3,4,5-tetrahydropyridazin-3-one; or g) 2-(4-butyrylaminobenzyl)-6-(3,4-dimethoxyphenyl)-5-ethyl-2,3,4,5-tetrahydropyridazin-3-one.

4. A process for the production of a pharmaceutical composition, comprising bringing a compound of the formula I according to claim 1 and/or one of its physiologically acceptable salts into a suitable dose form together with at least one solid, liquid or semi-liquid excipient or auxiliary.

5. A pharmaceutical composition comprising at least one compound of the formula I according to claim 1 and/or one of its physiologically acceptable salts and at least one solid, liquid or semi-liquid excipient or auxiliary.

6. A compound of claim 1, wherein R$^1$ is H, R$^2$ is H or A, and R$^3$ is OA.

7. A compound of claim 1, wherein R$^1$ is H, R$^2$ is methyl or ethyl, and R$^3$ and R$^4$ are each independently of one another OA.

8. A compound of claim 1, wherein R$^1$ is H, R$^2$ is H or A, and R$^3$ is OA, and R$^4$ is OA where A is mono-, di- or trifluoro-substituted alkyl having 1 to 6 C atoms.

9. A compound of claim 1, wherein R$^1$ is H, R$^2$ is methyl or ethyl, and R$^3$ and R$^4$ are each independently of one another OR$^{10}$.

10. A compound of claim 1, wherein R$^1$ and R$^2$ are each H, and R$^3$ and R$^4$ each independently of one another are OA.

* * * * *

UNITED STATES PATENT AND TRADEMARK OFFICE
CERTIFICATE OF CORRECTION

PATENT NO. : 6,399,611 B1
DATED : June 4, 2002
INVENTOR(S) : Rochus Jonas et al.

It is certified that error appears in the above-identified patent and that said Letters Patent is hereby corrected as shown below:

<u>Title page,</u>
Item [*], Notice, delete "0" and insert -- 922 --.

Signed and Sealed this

Twenty-third Day of March, 2004

JON W. DUDAS
*Acting Director of the United States Patent and Trademark Office*